US008889839B2

(12) United States Patent
de Bettencourt-Dias et al.

(10) Patent No.: US 8,889,839 B2
(45) Date of Patent: Nov. 18, 2014

(54) PYRIDINE-BIS (OXAZOLINE)("PYBOX") MOIETY AS A CHELATOR AND SENSITIZER FOR LANTHANIDE ION (LN (III)) LUMINESCENCE

(75) Inventors: Ana de Bettencourt-Dias, Reno, NV (US); Subha Viswanathan, Dallas, TX (US)

(73) Assignee: Syracuse University, Syracuse, NY (US)

( * ) Notice: Subject to any disclaimer, the term of this patent is extended or adjusted under 35 U.S.C. 154(b) by 1534 days.

(21) Appl. No.: 12/116,337

(22) Filed: May 7, 2008

(65) Prior Publication Data
US 2009/0281290 A1 Nov. 12, 2009

(51) Int. Cl.
*C07F 5/00* (2006.01)
*C07D 413/14* (2006.01)
*C07C 29/70* (2006.01)
*C07D 265/04* (2006.01)
*A61K 49/00* (2006.01)

(52) U.S. Cl.
CPC .............. *C07D 413/14* (2013.01); *C07C 29/70* (2013.01); *C07F 5/00* (2013.01); *C07D 265/04* (2013.01); *A61K 49/001* (2013.01); *A61K 49/0013* (2013.01)
USPC ............ 534/15; 424/1.11; 424/1.65; 424/9.1; 424/9.6

(58) Field of Classification Search
CPC . A61K 49/00; A61K 49/001; A61K 49/0013; A61K 49/0015; A61K 49/0021; A61K 49/0017; A61K 49/0019; A61K 49/0052; A61K 49/10; A61K 49/12; A61K 2123/00; A61K 2121/00; A61K 2121/00; C07D 265/00; C07D 265/04; C07D 265/06; C07D 265/08; C07D 265/10; C07D 413/14; C07F 5/00; C07F 5/003; C07C 29/70
USPC ............... 424/1.11, 1.53, 1.65; 534/7, 10–16; 548/100, 215; 546/1; 544/1, 63
See application file for complete search history.

(56) References Cited

U.S. PATENT DOCUMENTS

| 4,637,988 | A  | 1/1987  | Hinshaw        |
| 5,252,462 | A  | 10/1993 | Drevin         |
| 5,571,897 | A  | 11/1996 | Takalo et al.  |
| 5,622,821 | A  | 4/1997  | Selvin         |
| 5,639,615 | A  | 6/1997  | Selvin         |
| 5,656,433 | A  | 8/1997  | Selvin         |
| 6,337,944 | B1 | 1/2002  | Hofstraat      |
| 6,540,897 | B1 | 4/2003  | Mallia         |
| 6,544,437 | B2 | 4/2003  | Park           |
| 7,338,651 | B2 | 3/2008  | Bornhop        |
| 7,517,701 | B2 | 4/2009  | Parker         |
| 7,632,651 | B2 | 12/2009 | Boge           |
| 7,828,993 | B2 | 11/2010 | Roth           |

OTHER PUBLICATIONS

Desimoni et al (Journal of Organic Chemistry, 2003, vol. 68, No. 20, pp. 7862-7866).*
Bettencourt-Dias et al (J. Am. Chem. Soc., 2007, vol. 129, pp. 15436-15437).*
Vermonden et al (Tetrahedron, 2003, vol. 59, pp. 5039-5045).*
Desimoni et al (Eur. J. Org. Chem., 2004, pp. 3057-3062).*
Gans, et al., Investigation of equilibria in solution. Determination of equilibrium constants wit the HYPERQUAD suite of programs, Talanta,1996, 43, (10), 1739-1753.
Cantuel, et al., The First Enantiomerically Pure Helical Noncovalent Tripod for Assembling Nine-Coordinate Lanthanide(III) Podiates, Inorg. Chem. 2004, 43, 1840-1849.
Comby, et al., Influence of Anionic Functions on the Coordination and Photophysical Properties of Lanthanide(III) Complexes with Tridentate Bypyridines, Inorg. Chem. 2004, 43, 7369-7379.
Chen, et al., Selective Self-Assembly of Hexameric Homo- and Heteropolymetallic Lanthanide Wheels: Synthesis, Structure, and Phtophysical Studies, Inorg. Chem. 2007, 46 625-637.
Reinhard, et al., High-Resolution Optical Spectroscopy of Na[Ln(dpa)] 13HO with Ln=Er, Tm, Yb, Inorg. Chem. 2002, 41, (5), 1048-1055.
Jensen, et al., Lanthanide Triple-Stranded Helicates: Controlling the Yield of the Heterobimetallic Species, Inorg. Chem. 2006, 45, 7806-7814.
Petoud, et al., Luminescent Properties of Lanthanide Nitrato Complexes with Substituted Bis(benzimidazolyl)pyridines, Inorg. Chem. 1997, 36, 1345-1353.
Moore, et al., "*Cymothoe sangaris*": An Extremely Stable and Highly Luminescent 1,2-Hydroxypyridinonate Chelate of Eu(III), J. Am. Chem. Soc. 2006, 128, 10648-10649.
Petoud, et al., Brilliant Sm, Eu, Tb, and Dy Chiral Lanthanide Complexes with Strong Circularly Polarized Luminescence, J. Am. Chem. Soc. 2007, 129, 77-83.
Collis, et al., Toward Functionalized Conducting Polymers: Synthesis and Characterization of Novel β-Styryl)terthiophenes, J. Org. Chem. 2003, 68, (23), 8974-8983.
Klink, et al., Synergistic Complexation of Eu by a Polydentate Ligand and a Bidentate Antenna to Obtain Ternary Complexes with High Luminescence Quantum Yields, J. Phys. Chem. A 2002, 106, (15), 3681-3689.
Aspinall, et al., Lanthanide Pybox Complexes as Catalysts for Enantioselective Silylcyanation of Aldehydes, Organometallics 2005, 24, (14), 3458-3467.
Baldo, et al., Excitonic single-triplet ratio in a semiconducting organic thin film, Phys. Rev. B-Condensed Matter 1999, 60, (20), 14422-14428.
Patroniak, et al., Synthesis and Luminescence Properties of New Dinuclear Complexes of Lanthanide(III) Ions, Eur. J. Inorg. Chem. 2004, 2379-2384.
Desimoni, et al., A new and highly efficient catalyst for the enantioselective Mukaiyama-Michael reaction between (E)-3-crotonoyl-1,3-oxazolidin-2-one and 2-trimethylsilyloxyfuran, Tetrahedron 2001, 57, (51), 10203-10212.

(Continued)

*Primary Examiner* — D L Jones
(74) *Attorney, Agent, or Firm* — Frederick J. M. Price; George R. McGuire; Bond Schoeneck & King, PLLC

(57) ABSTRACT

This invention relates to novel Ln(III) complexes of pybox, and methods of making the same. The present invention also relates to a method of use of pybox as a chelating moiety and sensitizer for Ln(III) ion luminescence. Derivatives of pybox and methods of making the same are also provided.

2 Claims, 19 Drawing Sheets

(56) References Cited

OTHER PUBLICATIONS

Chauvin, et al., Europium and Terbium tris(Dipicolinates) as Secondary Standards for Quantum Yield Determination, Spectroscopy Lett. 2004, 37 (5), 517-532.

Aspinall, et al., Lanthanide complexes with $C_2$ symmetric ligands for use in enantio-selective organic synthesis, J. Alloys Compds. 2000, 303-304, 173-177.

Aspinall, et al., Defining effective chiral binding sites at lanthanides—highly enantio-selective reagents and catalysts from binaphtholate and pybox ligands, J. Organometal Chem. 2002, 647, (1-2), 151-157.

Charbonniere, et al., Anionically Substituted1,1'1''-Methylidynetris[1H-pyrazole] Ligands for the Formation of Neutral Lanthanide Complexes in Water: Synthesis, Characterization, and Photophysical Properties, Hely. Chim. Acta 2003, 86, 3402-3410.

Charbonniere, et al., Complexes of p-tert-butylcalix[5]arene with lanthanides: synthesis, structure and phtophysical properties, J. Chem. Soc., Dalton Trans. 1998, 505-510.

Chatteron, et al., An Efficient Design for the Rigid Assembly of Four Bidentate Chromophores in Water-Stable Highly Luminescent Lanthanide Complexes, Angew. Chem., Int. Ed. 2005, 44, 7595-7598.

Desimoni, et al., Pyridine-2, 6-bis(oxazolines), Helpful Ligands for Assymetric Catalysts, Chem. Rev. 2003, 103, (8), 3119-3154.

Crosby, et al., Intramolecular Energy Transfer in Rare Earth Chelates. Role of the Triplet State, J. Chem. Phys. 1961, 34, 743-748.

Edwards, et al., Photoluminescence and electroluminescence of new lanthanide-(methyoxybenzoyl)benzoate complexes, J. App. Phys. 1997, 82, 1841-1846.

Förster, Th., Excitation Transfer and Internal Conversion, Chem. Phys. Lett. 1971, 12, (2), 422-424.

* cited by examiner

Fig. 2

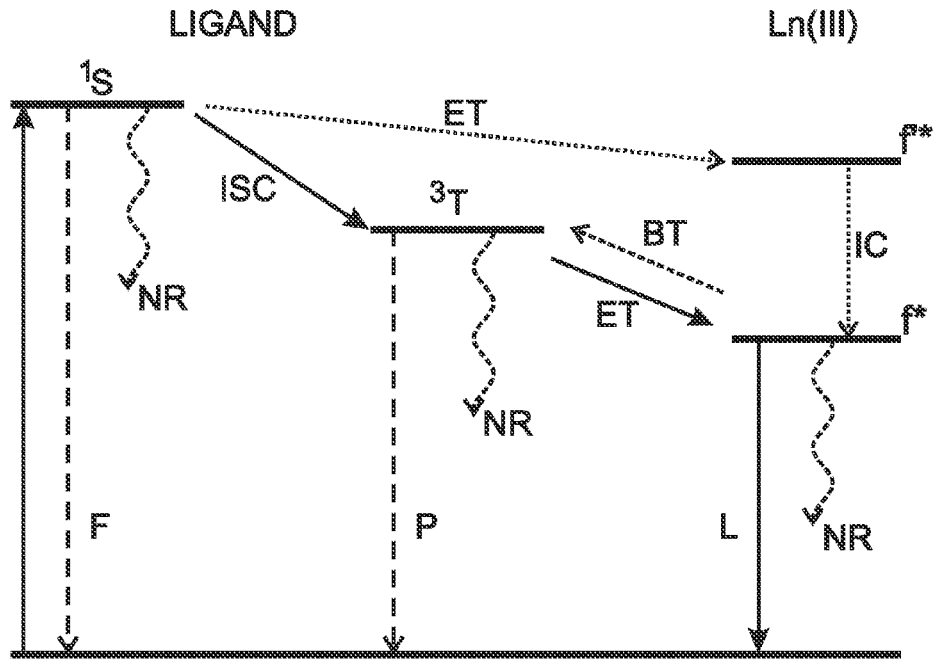

MECHANISM OF SENSITIZED EMISSION (SINGLET STATE $^1$S; TRIPLET STATE $^3$T; EXCITED STATE f*; RADIATIVE EXCITED STATE f*; FLUORESCENCE F; PHOSPHORESCENCE P; LUMINESCENCE L; NON-RADIATIVE PATHWAYS (NR); INTERSYSTEM CROSSING ISC; ENERGY TRANSFER ET; ENERGY BACKTRANSFER BT; INTERNAL CONVERSION IC; SOLID ARROWS - DESIRED ENERGY TRANSFER, DASHED ARROWS -POSSIBLE UNDESIRED ENERGY TRANSFER, DOTTED ARROWS -LESS LIKELY BUT POSSIBLE ENERGY TRANSFER).

Fig. 3

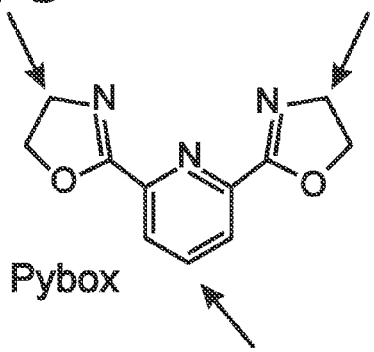

Pybox

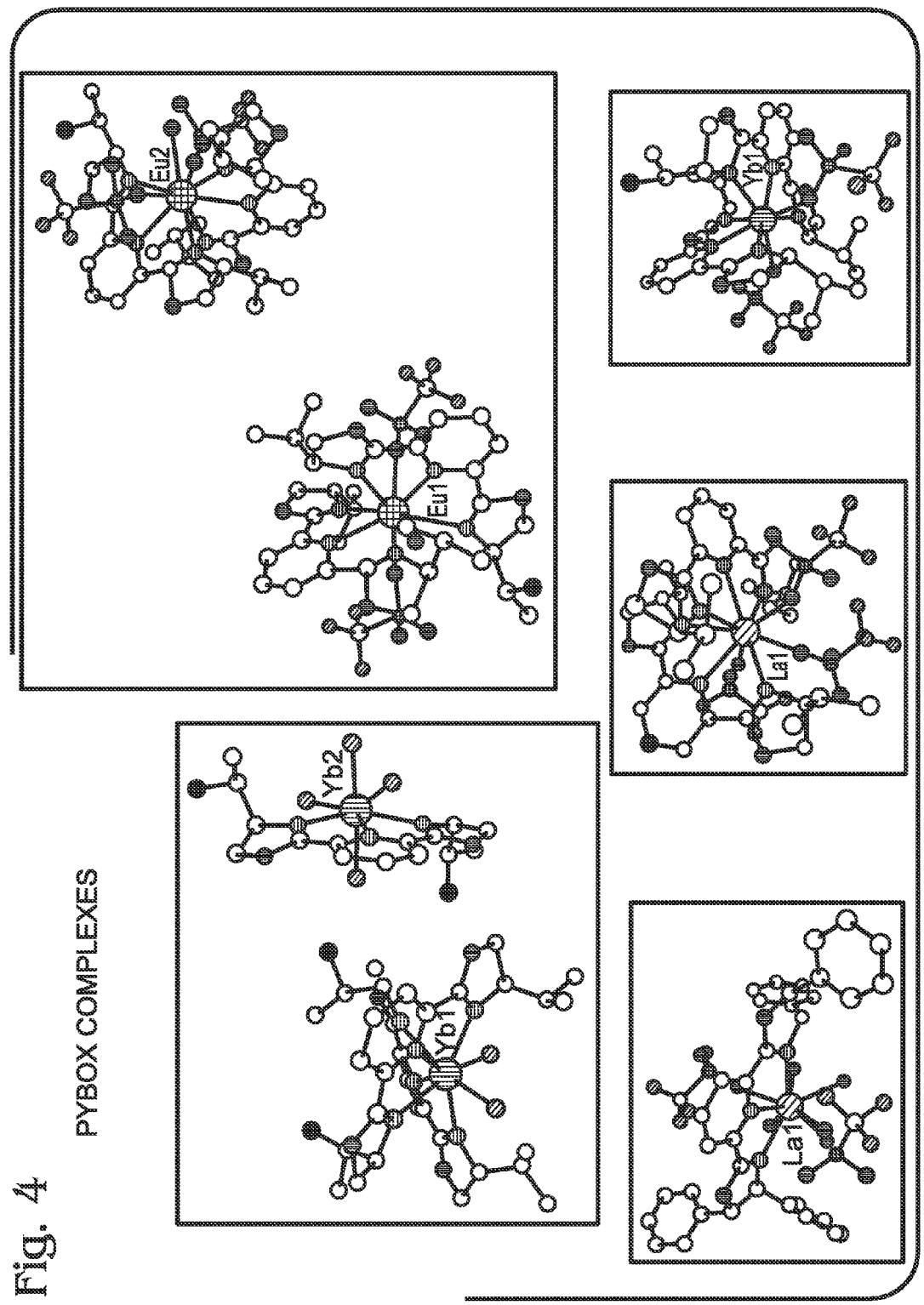
Fig. 4 PYBOX COMPLEXES

Structure OF [Eu(pybox-derivative)$_3$]$^{3+}$
calculated with CaChe
(MOPAC, AMI parameters).

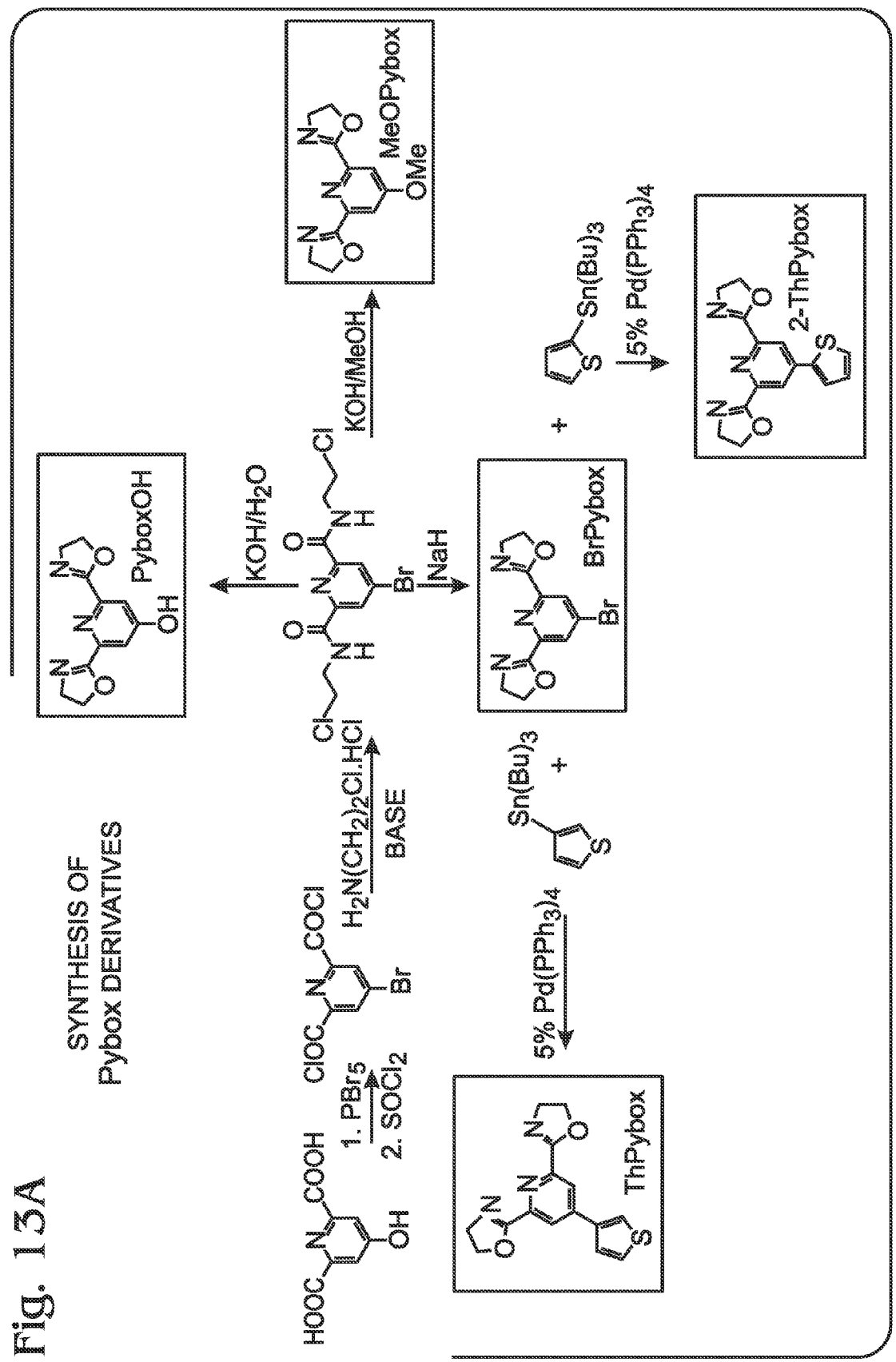
Fig. 13A SYNTHESIS OF Pybox DERIVATIVES

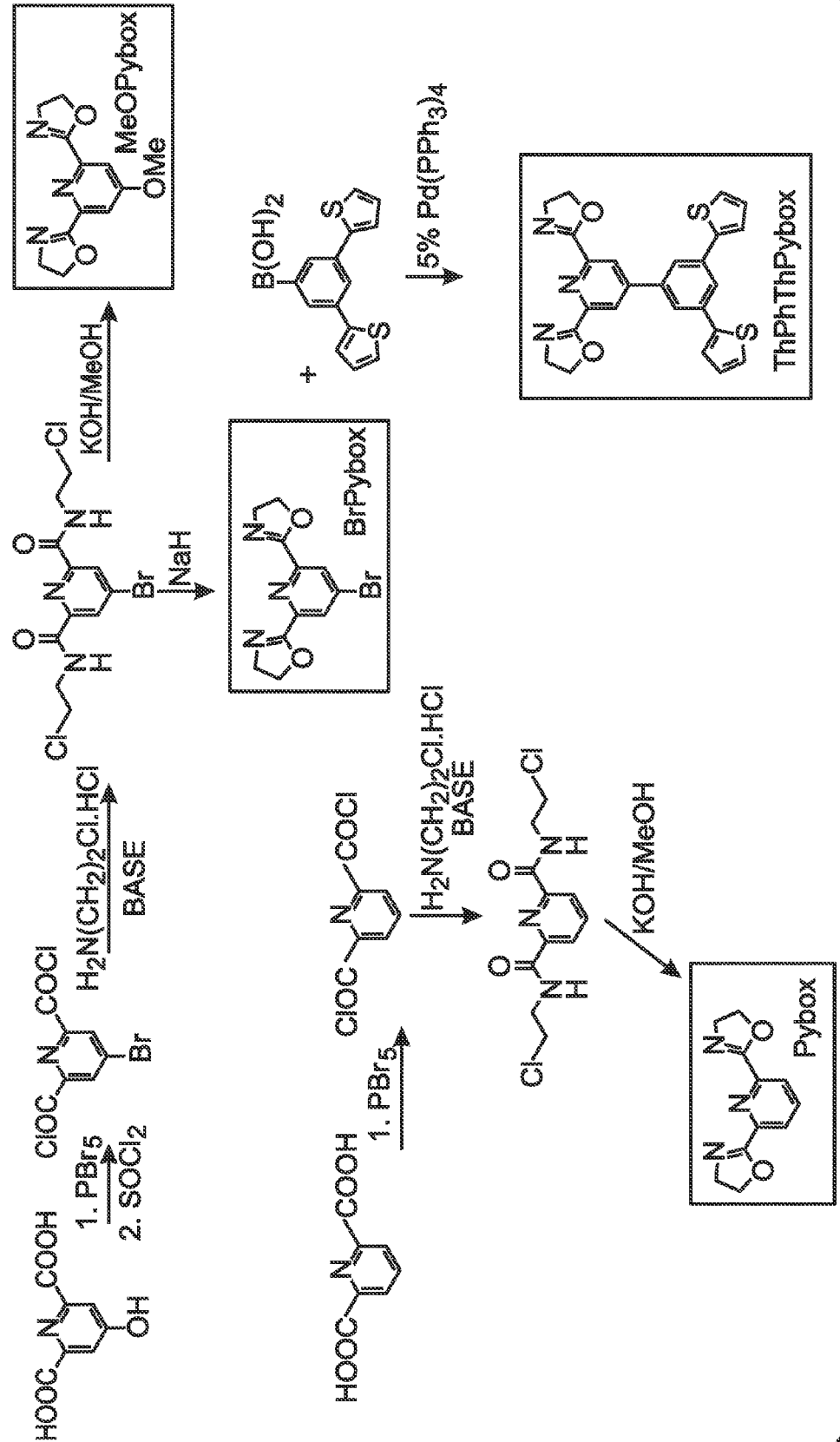
Fig. 13B SYNTHESIS OF Pybox DERIVATIVES

Fig. 14
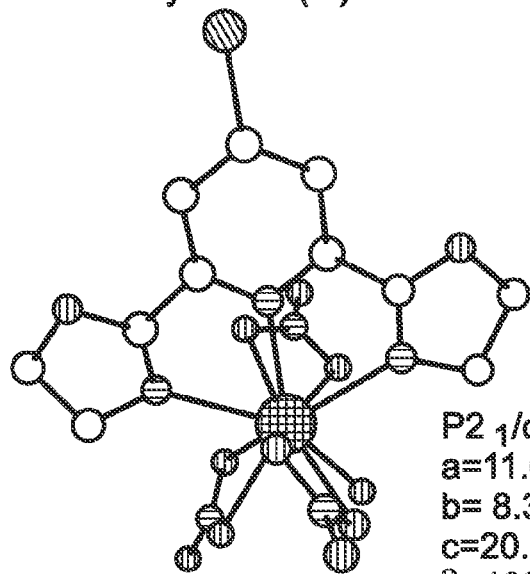
BrPybox-Eu(III)
P2₁/c
a=11.6485Å
b= 8.3914Å
c=20.3202Å
β=100.253°
V=1.954.536Å³
Fig. 17
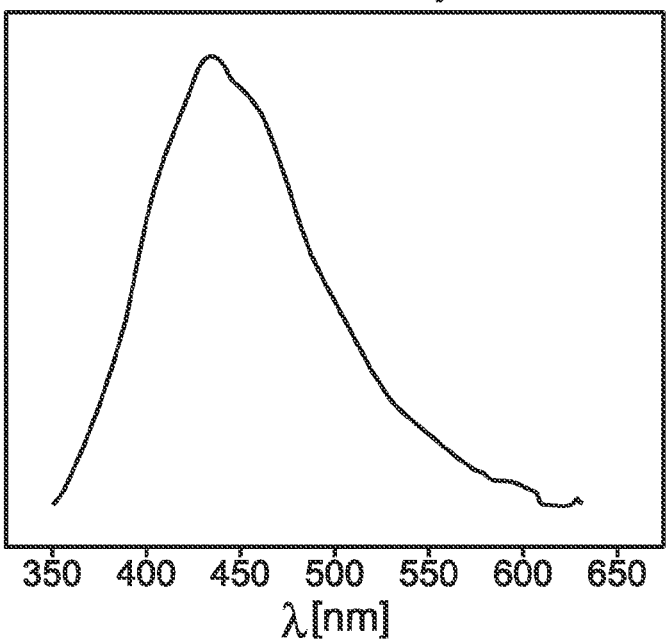
ThPybox
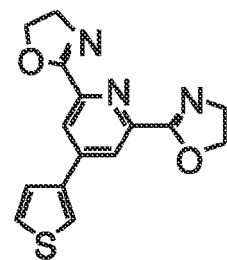

Fig. 21

SPECIATION AND PHOTOPHYSICS OF 3:1 COMPLEXES OF VARIOUS Pybox DERIVATIVES

| | | log β | φ [%] | τ [ms] | E($^1$S) [cm$^{-1}$] | E($^3$T) [cm$^{-1}$] |
|---|---|---|---|---|---|---|
| PyboxOMe | Eu | 4.61/6.59/11.17 | 82.0 | 2.173 | 32,790 | 25,110 |
| | Tb | 5.05/9.30/12.50 | 66.0 | 1.98 | | |
| PyboxBr | Eu | 7.04/12.56/16.74 | 69.2 | 1.461 | 31,060 | 23,980 |
| | Tb | 6.07/11.16/15.39 | 73.8 | 1.626/0.54 | | |
| PyboxTh | Eu | 5.07/10.70/15.38 | 83.7 | 1.540 | 28,310 | 21,080 |
| | Tb | 5.01/9.31/13.38 | 58.6 | 0.367/0.019 | | |
| Pybox | Eu | 5.22/9.74/13.46 | n.d. | n.d. | ~31,250 | 25,640 |
| | Tb | 4.15/8.11/12.81 | n.d. | n.d. | | |
| TjPhThPybox | Eu | n.d. | 49.0 | 0.436 | 26,540 | 21,850 |
| | Tb | n.d. | weak | weak | | |

PYRIDINE-BIS (OXAZOLINE)("PYBOX") MOIETY AS A CHELATOR AND SENSITIZER FOR LANTHANIDE ION (LN (III)) LUMINESCENCE

BACKGROUND OF THE INVENTION

1. Field of Invention

The present invention relates to the structure-property relationships between ligands and metal complexes and the efficiency of light emission, and, more specifically, to pyridine-bis(oxazoline) ("pybox") based ligands, lanthanide metal ion ("Ln (III)") complexes of pybox, and the use of pybox as a sensitizing moiety.

2. Description of the Related Art

Certain metal ions are of considerable interest due to their luminescent (light emission) characteristics, which arise from f-f transitions, e.g., any element from the lanthanide ("Ln") series including Eu(III), Tb(III) and Tm(III).

The brightness and unparalleled color purity of the emitted light from Ln(III) ions make these metal ions ideal components of the emitting layers in energy-efficient LEDs, as well as in applications such as fluoroimmunoassays, luminescent tags and sensors. (Bünzli, J.-C. G.; Choppin, G. R., *Lanthanide Probes in Life, Chemical and Earth Sciences—Theory and Practice. ed.*, Elsevier: Amsterdam, 1989, which is hereby incorporated by reference herein in its entirety. All other references cited to herein are hereby incorporated by reference herein in their respective entirety(ies).). Further, in contrast to organic emitters, Ln(III) ion emission has no theoretical limit with respect to its quantum yield. (Baldo, M. A.; O'Brien, D. F.; Thompson, M. E.; Forrest, S. R., *Phys. Rev. B-Condensed Matter* 1999, 60, (20), 14422-14428).

Ln(III) ion emission arises from intra-4f transitions. Since the 4f electrons are shielded from the ligand field by the 5s and 5p orbitals, the emission bands are largely independent of the coordination environment of the ion. Therefore, the emission bands are very sharp (full width at half maximum around 5 to 10 nm), yielding characteristic pure emission colors (see FIG. 1, illustrating the emission colors of Eu(III), Tb(III), and Tm(III)). However, the luminescence is Laporte (parity)-forbidden and spin-forbidden with low absorption coefficients. This means that population of the excited state of the Ln(III) ion will occur most efficiently by energy transfer from the excited state of a ligand as a sensitizer, or antenna, through a Förster-type mechanism. (Förster, T., *Chem. Phys. Lett.* 1971, 12, (2), 422-4.) This process is displayed in detail in FIG. 2, which is described in more detail infra.

As seen in FIG. 2, the ligand's singlet state is excited, and through inter-system crossing (ISC) it populates a triplet state. The triplet state can subsequently transfer energy (ET) to a coordinated Ln(III) ion, which will ultimately luminesce. The quantum yield of metal-centered luminescence upon excitation $Q_L^{Ln}$ depends on the efficiency of these individual steps and is summarized in the following equation:

$$Q_L^{Ln} = \eta_{ISC} \times \eta_{ET} \times Q_{Ln}^{Ln}$$

where $\eta_{ISC}$ is the efficiency of intersystem crossing from the singlet to the triplet state of the ligand, $\eta_{ET}$ the efficiency of the energy transfer from the triplet state to the Ln(III) ion excited state, and $Q_{Ln}^{Ln}$ is the intrinsic quantum yield of the Ln(III) ion emission upon direct excitation. (Chauvin, A.-S.; Gumy, F.; Imbert, D.; Bünzli, J.-C. G., *Spectroscopy Lett.* 2004, 37, (5), 517-532.)

For an efficient ISC, a gap of approximately 5000 cm$^{-1}$ between the singlet and triplet states is required. For an efficient ET, the antenna triplet state must be higher in energy than the 4f excited state by about 2,500 to 4,000 cm$^{-1}$ (otherwise back transfer (BT) is likely to occur), and the ligand should be directly coordinated to the metal ion. (Klink, S. I.; Hebbink, G. A.; Grave, L.; Oude Alink, P. G. B.; van Veggel, F. C. J. M.; Werts, M. H. V., *J. Phys. Chem. A* 2002, 106, (15), 3681-3689.) (Reinhard, C.; Güdel, H. U., *Inorg. Chem.* 2002, 41, (5), 1048-1055.) Non-radiative (NR) deactivation of the 4f excited state through lattice, O—H, C—H or N—H vibrations, as well as ligand fluorescence (F), phosphorescence (P) or NR deactivation can decrease the quantum yield of Ln-centered emission and should be prevented through careful system design.

Numerous ligand designs have been described, from simple 2,6-pyridinedicarboxylic acid, shown to sensitize near-IR emission of Yb(III) (see Reinhard, C.; Güdel, H. U. *Inorg. Chem.* 2002, 41, 1048-1055), and utilized in standards for the determination of quantum yields of emission (see Chauvin, A.-S.; Gumy, F.; Imbert, D.; Bünzli, J.-C. G. *Spectroscopy Lett.*, 2004, 37, 517-532), to more complex chelating architectures, capable of discriminating between different lanthanide ions and of yielding complexes with high quantum yields of luminescence. (Jensen, T. B.; Scopelliti, R.; Bünzli, J.-C. G. *Inorg. Chem.* 2006, 45, 7806-7814; Moore, E. G.; Xu, J.; Jocher, C. J.; Werner, E. J.; Raymond, K. N. *J. Am. Chem. Soc.* 2006, 128, 10648-10649). A chelating architecture, or complex, relates to the binding of two or more atoms of a chelator or chelating agent (i.e., a multidentate ligand—a ligand that is capable of donating two or more pairs of electrons in a complexation reaction to form coordinate bonds) with a metal ion.

Pyridine-2,6-bis(oxazoline) or pybox (see FIG. 3), since its first description in 1989, has been the focus of attention as a ligand for coordination complexes in asymmetric catalysis. (Desimoni, G.; Faita, G.; Quadrelli, P., *Chem. Rev.* 2003, 103, (8), 3119-3154.) The coordination ability of pybox has been documented. Desimoni and co-workers have isolated a 1:1 complex with La(III), in which the coordination sphere of the metal ion is completed with triflate counter-anions and water molecules. (Desimoni, G.; Faita, G.; Filippone, S.; Mella, M.; Zampori, M. G.; Zema, M., *Tetrahedron* 2001, 57, (51), 10203-10212.) Aspinall and co-workers isolated 2:1 complexes, which also contain solvent molecules and counter-anions to complete the coordination sphere of the metal ion. (Aspinall, H. C.; Dwyer, J. L. M.; Greeves, N.; Smith, P. M., *J. Alloys Compds.* 2000, 303-304, 173-177.) (Aspinall, H. C.; Bickley, J. F.; Greeves, N.; Kelly, R. V.; Smith, P. M., *Organometallics* 2005, 24, (14), 3458-3467.) They also observed that these complexes are stable in solution, since no exchange is seen by NMR between coordinated pybox ligands and free ligand present in excess in solution. (Aspinall, H. C.; Greeves, N., *J. Organometal. Chem.* 2002, 647, (1-2), 151-157).

Although pybox and its derivatives were extensively utilized by Aspinall and co-workers as well as Desimoni and co-workers (see Aspinall, H. C.; Bickley, J. F.; Greeves, N.; Kelly, R. V.; Smith, P. M. *Organometallics* 2005, 24, 3458-3467; Aspinall, H. C.; Dwyer, J. L. M.; Greeves, N.; Smith, P. M. *J. Alloys Compds.* 2000, 303-304, 173-177; Aspinall, H. C.; Greeves, N. *J. Organomet. Chem.* 2002, 647, 151-157; Desimoni, G.; Faita, G.; Filippone, S.; Mella, M.; Zampori, M. G.; Zema, M. *Tetrahedron* 2001, 57, 10203-10212;) in lanthanide ion complexes for enantioselective catalysis (see FIG. 4, illustrating previously described pybox complexes) pybox and its derivatives have never been reported as sensitizers for lanthanide luminescence. The pybox ligand is extremely versatile, as it allows straightforward derivatization of the para position of the pyridine ring, as well as of the carbon atoms of the oxazoline ring. (See Aspinall, H. C.;

Bickley, J. F.; Greeves, N.; Kelly, R. V.; Smith, P. M. *Organometallics* 2005, 24, 3458-3467; Aspinall, H. C.; Dwyer, J. L. M.; Greeves, N.; Smith, P. M. *J. Alloys Compds.* 2000, 303-304, 173-177; Aspinall, H. C.; Greeves, N. *J. Organomet. Chem.* 2002, 647, 151-157; Desimoni, G.; Faita, G.; Filippone, S.; Mella, M.; Zampori, M. G.; Zema, M. *Tetrahedron* 2001, 57, 10203-10212; Desimoni, G.; Faita, G.; Quadrelli, P. *Chem. Rev.* 2003, 103, 3119-3154). As seen in FIG. 3, arrows point out the carbon atoms which can be further derivatized.

Accordingly, very little structural information is known about Ln(III) ion complexes with the pybox ligand, and no description of the pybox ligand's sensitization capabilities has been made, as the research efforts have focused on the catalytic capabilities of the complexes.

BRIEF SUMMARY OF THE INVENTION

It is therefore a principal object and advantage of the present invention to improve quantum yields of photoluminescence and develop new compounds with purer emission colors, longer operation lifetimes and better energy efficiency.

It is a further object and advantage of the present invention to develop and screen these compounds for application in LED technology, as well as for other fields of application including fluoroimmunoassays, luminescent tags and sensors.

In accordance with the foregoing objects and advantages, the present invention provides novel Ln(III) complexes of pybox, and methods of making the same. The present invention also provides a method of using pybox and derivatives of pybox as a chelating moiety and sensitizer for Ln(III) ion luminescence.

Furthermore, in accordance with an embodiment of the present invention, derivatives of pybox and methods of making the same are provided.

BRIEF DESCRIPTION OF THE DRAWINGS

The present invention will be more fully understood and appreciated by reading the following Detailed Description in conjunction with the accompanying drawings, in which:

FIG. 2 is a graphical illustration of the mechanism of sensitized emission, according to an embodiment of the present invention.

FIG. 3 is a high level schematic illustrating pybox, with arrows showing the carbon atoms which can be further derivatized, according to an embodiment of the present invention.

FIG. 4 is a high level schematic illustrating pybox complexes previously described in the literature.

FIG. 7a-b shows partial ball-and-stick drawings illustrating the F—O short contacts and weak hydrogen bonding interactions C—H—F in the 2:1 ThPybox-Eu(III) complex, according to an embodiment of the present invention.

FIGS. 13a-c are high level schematics illustrating ligand synthesis (e.g., pybox derivatives), according to an embodiment of the present invention.

FIG. 14 is a high level schematic illustrating a BrPybox-Eu(III) complex, according to an embodiment of the present invention.

FIG. 17 is a graphical illustration which shows the blue fluorescence at λ~430 nm of a pybox ligand derivatized with thiophene at the para position of the pyridine ring, according to an embodiment of the present invention.

FIG. 21 is a table representation illustrating speciation and photophysics of 3:1 complexes of various pybox derivatized ligands including BrPybox and MeOPybox, complexed with Ln (III) metal ions including Eu and Tb, according to an embodiment of the present invention.

DETAILED DESCRIPTION OF THE INVENTION

Figure 1:
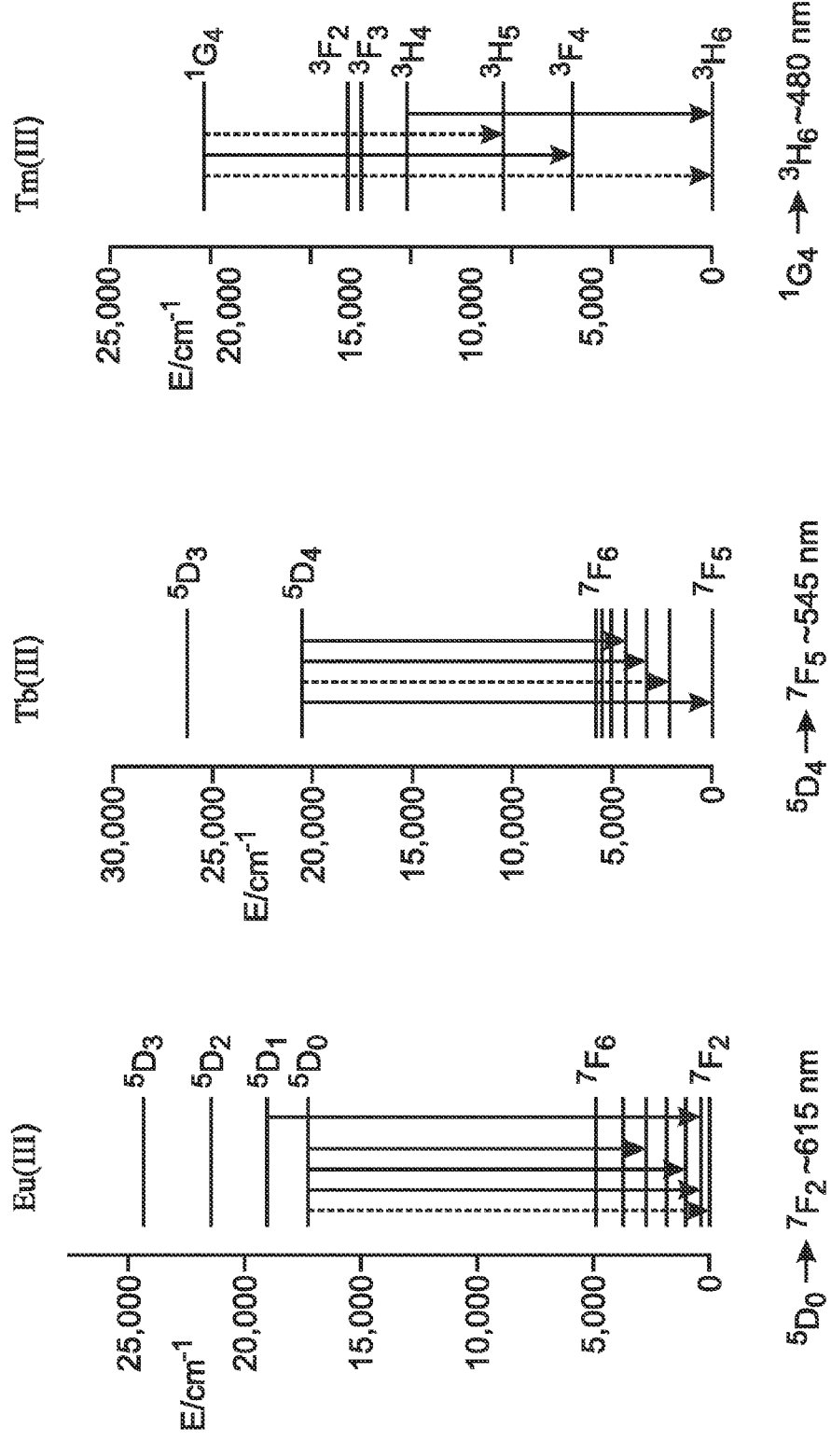
FIG. 1 is a graphical illustration of the emission colors of Eu(III), Tb(III), and Tm(III) according to an embodiment of the present invention.

The present invention will be more fully understood and appreciated by reading the following Detailed Description in conjunction with the accompanying drawings, wherein like reference numerals refer to like components.

In accordance with an embodiment of the present invention, the use of pybox as sensitizer is provided. The isolation of highly luminescent complexes of Ln(III) ions with thiophene-derivatized-pybox (4-thiophen-3-yl-pyridine-2,6-bis(oxazoline) ("ThPybox"), is described. For instance, as described further in the Examples infra, a new complex of ThPybox with Eu(III) triflate has been isolated. This complex and its Tb(III) analogue are luminescent in the solid state.

Additionally, as described further in the Examples infra, these complexes dissolve with partial retention of the solid-state structure in acetonitrile to yield highly luminescent solutions with significant quantum yields. Specifically, highly luminescent solutions were obtained upon dissolution of the ligand in acetonitrile with $Ln(CF_3SO_3)_3$ in 3:1 stoichiometry, with quantum emission values of 76.2% for Ln=Eu and 58.6% for Ln=Tb. Preliminary studies with other synthesized pybox derivatives also showed a yield of highly luminescent solutions (see FIG. 21 for a table representation illustrating speciation and photophysics of 3:1 complexes of various Pybox derivatized ligands including BrPybox and MeOPybox, complexed with Ln (III) metal ions including Eu and Tb).

The Eu(III) emission quantum yield efficiency with ThPybox as the sensitizer, as described herein, was shown to surpass complexes recently described for which emission quantum yields in water were 21.5%-25.5% (Moore, E. G.; Xu, J.; Jocher, C. J.; Werner, E. J.; Raymond, K. N. *J. Am. Chem. Soc.* 2006, 128, 10648-10649; Chen, X.-Y.; Bretonniere, Y.; Pecaut, J.; Imbert, D.; Bünzli, J.-C.; Mazzanti, M. *Inorg. Chem.* 2007, 46, 625-637), 16% in $CH_2Cl_2$ (Edwards, A.; Claude, C.; Sokolik, I.; Chu, T. Y.; Okamoto, Y.; Dorsinville, R. *J. Appl. Phys.* 1997, 82, 1841-1846), and 2.3% in MeOH (Petoud, S.; Muller, G.; Moore, E. G.; Xu, J.; Sokolnicki, J.; Riehl, J. P.; Le, U. N.; Cohen, S. M.; Raymond, K. N. *J. Am. Chem. Soc.* 2007, 129, 77-83).

The efficiency for Tb(III), as described herein, is also high and compares favorably with recently described systems, with values of 15%-45.5% in water (Charbonniere, L. J.; Ziessel, R. *Helv. Chim. Acta* 2003, 86, 3402-3410; Comby, S.; Imbert, D.; Chauvin, A.-S.; Bünzli, J.-C. G.; Charbonniere, L. J.; Ziessel, R. F. *Inorg. Chem.* 2004, 43, 7369-7379; Chatterton, N.; Bretonniere, Y.; Pecaut, J.; Mazzanti, M. *Angew. Chem., Int. Ed.* 2005, 44, 7595-7598), 5.1% in THF (Charbonniere, L. J.; Balsiger, C.; Schenk, K. J.; Bünzli, J.-C. G. *J. Chem. Soc., Dalton Trans.* 1998, 505-510), 27% in $CH_2Cl_2$ (Edwards, A.; Claude, C.; Sokolik, I.; Chu, T. Y.; Okamoto, Y.; Dorsinville, R. *J. Appl. Phys.* 1997, 82, 1841-1846), and 63% in MeOH (Petoud, S.; Muller, G.; Moore, E. G.; Xu, J.; Sokolnicki, J.; Riehl, J. P.; Le, U. N.; Cohen, S. M.; Raymond, K. N. *J. Am. Chem. Soc.* 2007, 129, 77-83). In the solvent acetonitrile, quantum yields of 1.3 and 4.7%, respectively, were reported for $[Ln(terpy)_3]^{3+}$ (Ln=Eu, Tb) (Charbonniere, L. J.; Balsiger, C.; Schenk, K. J.; Bünzli, J.-C. G. *J. Chem. Soc., Dalton Trans.* 1998, 505-510; Petoud, S.; Bünzli, J.-C. G.; Schenk, K. J.; Piguet, C. *Inorg. Chem.* 1997, 36, 1345-1353).

The excellent sensitization ability coupled with the versatility in derivatization makes this family of pybox-based ligands very appealing for designing luminescent lanthanide ion complexes. The photophysical characterization of the luminescent solutions of Eu(III) and Tb(III) with ThPybox is described herein, along with X-ray crystallographic characterization. Solution speciation and spectroscopic details are also described.

Several chelators appropriate for coordinating Ln(III) ions and forming 1:1 and 2:1 complexes with pybox and its derivatives were developed, as discussed infra. Additionally, the existence of 3:1 complexes with pybox and its derivatives was shown by spectroscopic methods.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

With respect to the following examples, NMR spectra were recorded either on a Bruker DRX-500 or a Bruker Avance DPX 300 spectrometer. UV spectra were recorded on a Perkin Elmer Lambda 35 and fluorescence spectra on a Perkin Elmer LS-55 spectrometer. Emission lifetimes were measured on the Perkin Elmer LS-55 utilizing the Short Phosphorescence Decay software package. All commercially obtained reagents were of analytical grade and used as received. Solvents were dried by standard methods. Lanthanide salts were either used as available or dried under reduced pressure and heating and kept in a glove box under controlled atmosphere ($O_2$<2 ppm, $H_2O$<5 ppm). All data were collected at a constant temperature of 25.0±0.1° C.

EXAMPLE 1

This Example shows the synthesis of a thiophene-derivatized-pybox (4-thiophen-3-yl-pyridine-2,6-bis(oxazoline)), ThPybox, through modified literature procedures in 7% overall yield from chelidamic acid. Scheme 1, set forth and described in detail in the following Examples, shows the synthesis of the ligand ThPybox as follows:

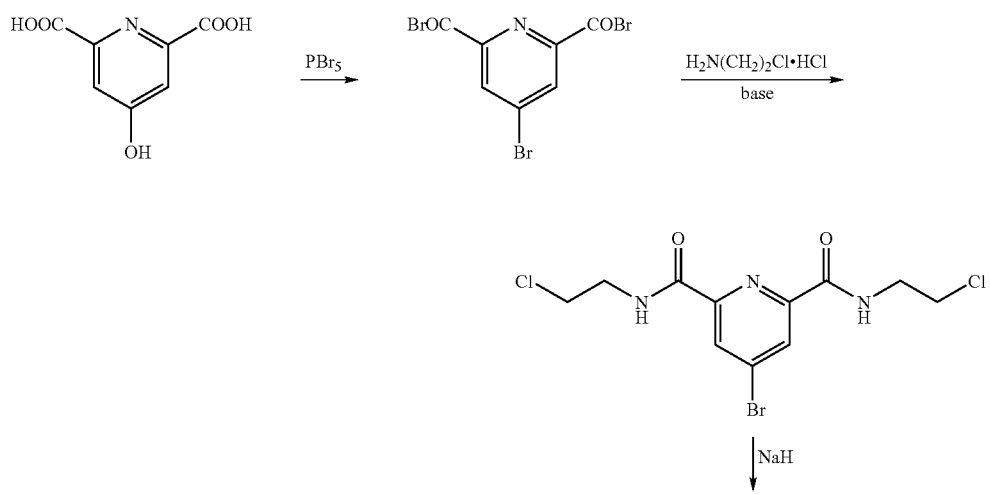

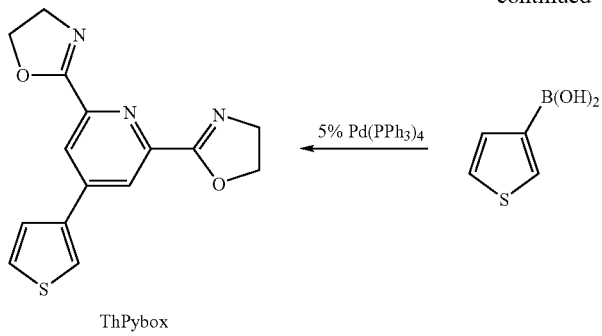

ThPybox

EXAMPLE 2

This Example describes the synthesis of 4-bromopyridine-2,6-dicarbonyl dibromide as shown below:

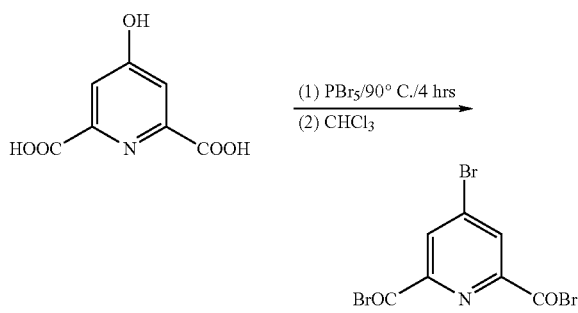

In a first step, PBr$_3$ (F.W.=270.7 g/mol, d=2.852 g/ml, 0.1788 mol=48.4 g or 17 ml) was added to a vigorously stirred solution of bromine (0.1476 mol=23.6 g or 7.68 ml) in petroleum ether (~50 ml). After stirring the mixture at room temperature for one hour, PBr$_5$ was obtained in pure form by removing excess petroleum ether by decantation after repeated washings. After drying in vacuo, chelidamic acid (54.6 mmol=10 g) was added and the resulting solid mixture was heated to 90° C. for 3-4 hours. After cooling down to room temperature, 20 ml of chloroform was added, and the mixture was stirred for 30 minutes and then filtered ($^1$H-NMR (CDCl$_3$): δ 8.38 [2H, s]). Yield of the 4-bromopyridine-2,6-dicarbonyl dibromide=80.0%.

EXAMPLE 3

This Example describes the synthesis of 4-bromo-bis(2-chloromethyl)pyridine-2,6-dicarboxamide as shown below:

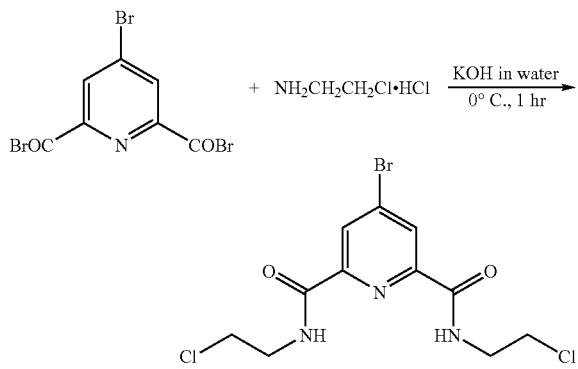

A solution of the crude acid bromide prepared in Example 2 in chloroform (~50 ml) was added to a solution of NH$_2$CH$_2$CH$_2$Cl·HCl (21 mmol=2.45 g) and KOH (40 mmol=2.3 g) in water (~30 ml) at 0° C. The resulting solution was stirred for an hour at 0° C., filtered, washed with water and dried on the pump to provide crude 4-bromo-bis(2-chloroethyl)pyridine-2,6-dicarboxamide as a white powder ($^1$H-NMR (CDCl$_3$): δ 3.78 [4H, t, $_3$J=9.6 Hz], 4.55 [4H, q, $_3$J=9.6 Hz], 8.39 ppm [2H, s]). Yield of the 4-bromo-bis(2-chloromethyl)pyridine-2,6-dicarboxamide=72.0%.

EXAMPLE 4

This Example describes the synthesis of 4-bromopyridine-2,6-bis(oxazoline) as shown below:

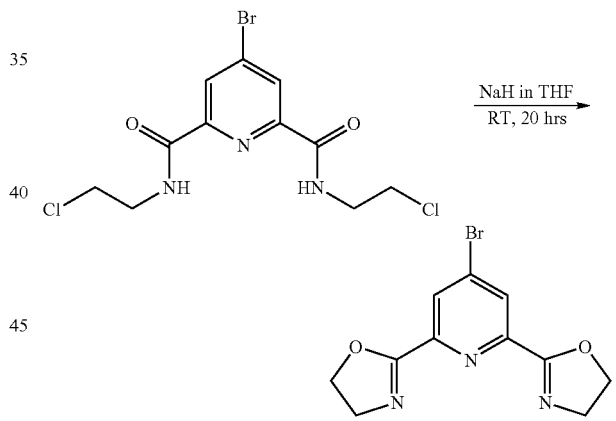

A solution of the crude amide in ~25 ml THF was added to a suspension of NaH (0.4 g of 60% suspension in mineral oil, 10 mmol) in THF (50 ml) at 0° C. The reaction mixture was stirred over 20 hours, and then quenched by HCl. Most of the THF was evaporated, ethyl acetate was added and the resulting solution was washed with brine, water, dried over anhydrous MgSO$_4$ and concentrated. The residue was recrystallized from ethanol to provide 4-bromo-2,6-bis(4,5-dihydrooxazol-2-yl)-pyridine as a white crystalline solid. ($^1$H-NMR (CDCl$_3$): δ 4.10 [4H, t, $_3$J=9.6 Hz], 4.52 [4H, t, $_3$J=9.6 Hz], 8.39 ppm [2H, s]. Yield of 4-bromopyridine-2,6-bis(oxazoline)=54.0%. Overall yield for three steps=30.2%.

EXAMPLE 5

This Example describes the synthesis of thiophene-3-boronic acid as shown below:

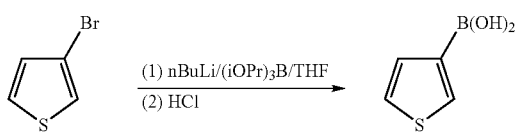

A solution of 3-bromothiophene (30.67 mmol=5 g) and tri-isopropyl borate (40 mmol=8.33 g or 9 ml) in 30 ml THF was treated with n-BuLi (2.5M in hexanes, 40 mmol 16 ml) at −78° C. over a period of 20 minutes. The resulting solution was stirred at −78° C. for an hour, and was then warmed up to −20° C. slowly and quenched slowly using 2N HCl. The mixture was then warmed to room temperature, diluted with ethyl acetated and brine. The organic layer was separated, concentrated and dried in vacuo. The white crude residue was re-crystallized using hot water to give 2.25 g of pure thiophene-3-boronic acid (17.58 mmol, 57.3%) with m.p at 126-128° C. [128-130° C. reported] (see Collis, G. E.; Burrell, A. K.; Scott, S. M.; Officer, D. L., *J. Org. Chem.* 2003, 68, (23), 8974-8983).

EXAMPLE 6

This Example describes the synthesis of 4-thiophen-3-yl-pyridine-2,6-bis(oxazoline) as shown below:

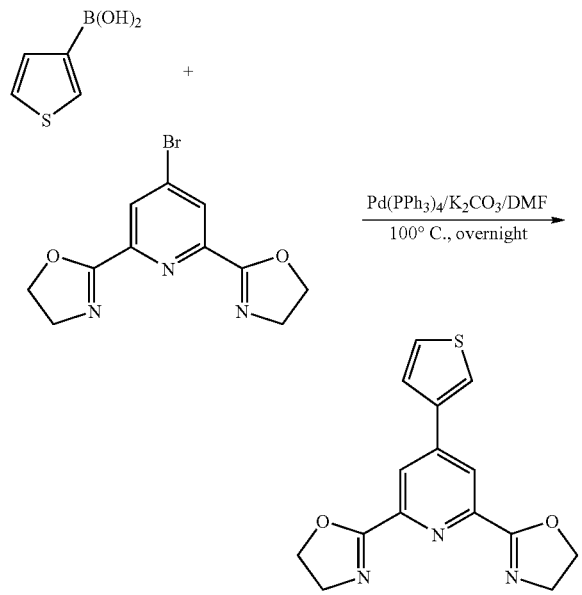

A suspension of thiophene-3-boronic acid (1.0 g, 7.81 mmol) obtained in Example 5, 4-bromo-2,6-bis(4,5-dihydro-oxazol-2-yl)-pyridine (2.31 g, 7.81 mmol), $K_2CO_3$ (3.28 g, 32.43 mmol), $Pd(PPh_3)_4$ (0.18 g, 0.16 mmol) in 20 ml DMF was stirred overnight at 105° C. The reaction mixture was cooled to room temperature, poured into water and extracted with ethyl acetate. The combined organic layers were washed with brine and water, dried over anhydrous $MgSO_4$ and concentrated. The residue was chromatographed over silica gel using $CH_2Cl_2$:MeOH (1:15) to provide 0.45 g (1.49 mmol, 19%) of 4-thiophen-3-yl-pyridine-2,6-bis(oxazoline) as a white solid ($^1$H-NMR (CDCl$_3$): δ 4.11 [4H, t, 3J=9.6 Hz], 4.52 [4H, t, 3J=9.6 Hz], 7.44 [1H, dd, 3J=3.0, 5.1 Hz], 7.53 [1H, dd, 3J=1.5, 5.1 Hz], 7.82 [1H, dd, 3J=1.5, 3.0 Hz], 8.37 ppm [2H, s]; $^{13}$C-NMR (CDCl$_3$): δ 55.0, 68.2, 122.2, 124.3, 125.3, 127.0, 137.8, 144.0, 147.2, 163.5 ppm). Yield of the 4-thiophen-3-yl-pyridine-2,6-bis(oxazoline) ("ThPybox ligand")=19%.

EXAMPLE 7

This Example describes the use of the derivatized pybox obtained in Example 6, ThPybox, as a sensitizer, and the isolation of a highly luminescent complex of ThPybox with a lanthanide ion, Eu(CF$_3$SO$_3$)$_3$.

In a first step, crystallographic characterization of this complex was obtained by stirring ThPybox with Eu(CF$_3$SO$_3$)$_3$ in 1:1 MeOH/CH$_3$CN. X-ray quality crystals of a 2:1 metal complex were produced within a few days.

Suitable crystals for data collection were mounted on a glass fiber and placed in the low-temperature nitrogen stream. Data were collected on a Bruker SMART CCD area detector diffractometer equipped with a low-temperature nitrogen device, using graphite-monochromated Mo—Kα radiation (λ=0.71073 Å). Data were measured using omega scans of 0.3° per frame and a full sphere of data was collected, for a total of 1850 frames. The first 50 frames were recollected at the end of the data collection to monitor for decay. Cell parameters were retrieved using SMART software (*SMART: v. 5.626, Bruker Molecular Analysis Research Tool*, Bruker AXS: Madison, Wis., 2002) and refined using SAINTPlus (*SAINTPlus: v. 6.36a, Data Reduction and Correction Program*, Bruker AXS: Madison, Wis., 2001) on all observed reflections. Data reduction and correction for Lp and decay were performed using SAINTPlus$_7$ software. Multi-scan absorption corrections were applied using SADABS (*SADABS: v. 2.01, an empirical absorption correction program*, Bruker AXS: Madison, Wis., 2001).

The structure was solved by direct methods and refined by least-squares methods on F$_2$ using SHELXTL program package (*SHELXTL: v. 6.10, Structure Determination Software Suite*, Sheldrick, G. M., Bruker AXS: Madison, Wis., 2001). All non-hydrogen atoms were refined anisotropically. The hydrogen atoms were added geometrically and their parameters constrained to the parent site. For the complex described here, hydrogen atoms of the water molecules coordinated to the metal center could not be located on the difference map and have been omitted, although the correct formula are indicated.

Finally, one of the triflate anions is highly disordered. Its atoms were therefore restrained and left isotropic. The two thiophene moieties in the complex are also disordered due to free rotation around the C—C bond between the thiophene and the pyridine rings. The disorder was modeled by allowing two components which are rotated by 180° from each other. The main component for the thiophene ring involving atom S1 displays ~75% occupancy and in the case of the thiophene ring with atom S2 the occupancy is ~52%. The disorder in this molecule, both from the thiophene rings as well as the triflate counter-ion leads to slightly enlarged thermal parameters.

The crystallographic data, data collection, and refinement details for the Eu(III) complex of ThPybox is given in Table S1 below.

TABLE S1

Crystallographic details for the 2:1 complex of ThPybox with Eu(III).

| Complex | ThPybox-Eu |
|---|---|
| Formula | $C_{33}H_{26}EuF_9N_6O_{16}S_5$ |
| M/g mol$^{-1}$ | 1245.86 |

TABLE S1-continued

Crystallographic details for the 2:1 complex of ThPybox with Eu(III).

| Complex | ThPybox-Eu |
|---|---|
| Crystal system | Monoclinic |
| Space group | C2/c |
| a/Å | 16.840(3) |
| b/Å | 16.541(4) |
| c/Å | 16.309(3) |
| β/° | 104.57(3) |
| V/Å$^3$ | 4396.5(16) |
| T/K | 101(2) |
| Z | 4 |
| $D_c$/g cm$^{-3}$ | 1.882 |
| μ(Mo-Kα)/mm$^{-1}$ | 1.779 |
| Independent reflections, $R_{int}$ [$F_o \geq 4\sigma(F_o)$] | 3981, 0.0328 |
| Reflections collected | 18094 |
| Data/restraints/parameters | 3981/23/306 |
| Goodness-of-fit on F$^2$ | 1.059 |
| $R_1$, w$R_2$ (all data) | 0.0547, 0.1373 |
| Largest diff. peak and hole/e · Å$^{-3}$ | 1.720, −1.676 |

Figure 5A:
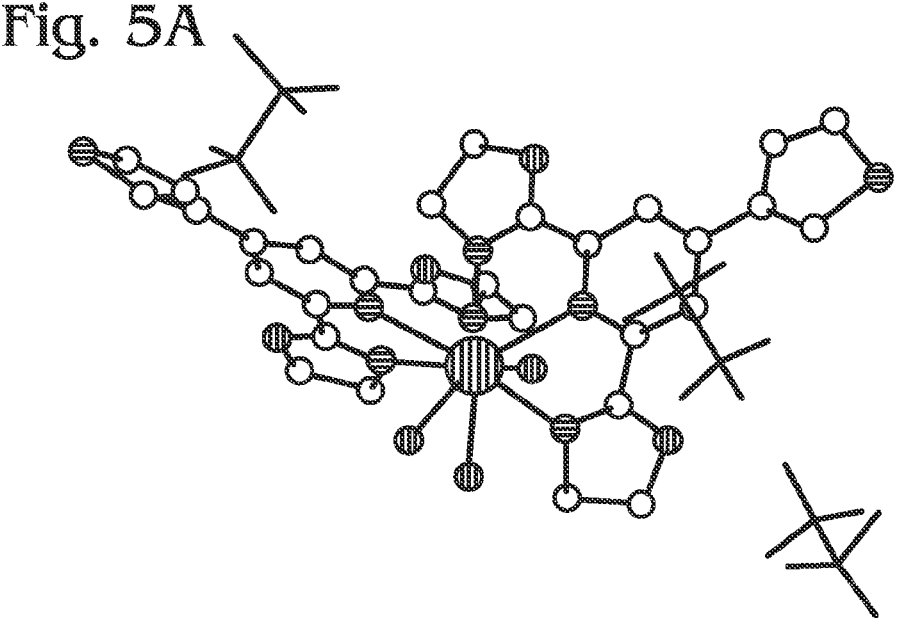
FIG. 5a is a ball-and-stick and wire diagram of pybox derivatized with thiophen-3-yl (ThPybox) with $Eu(CF_3SO_3)_3$ (ThPyboxEu) according to an embodiment of the present invention.

As seen in FIG. 5a, a ball-and-stick and wire diagram of ThPybox with Eu(CF$_3$SO$_3$)$_3$ is provided. While the isolation of a 2:1 ligand-to-metal complex with this ligand has been described herein, depending on the initial ligand-to-metal ion stoichiometry in solution, complexes with different stoichiometries were isolated with other pybox derivatives (see FIG. 13d).

The results show that the ThPybox with Eu(CF$_3$SO$_3$)$_3$ complex discussed in this Example crystallizes in the monoclinic space group C2/c, with one ligand and 1.5 water molecules coordinated to the Eu(III) as well as 1.5 noncoordinated triflate ions in the asymmetric unit. The remaining coordination sphere and counter-ions are generated by symmetry.

Eu(III) has a coordination number of nine and is bound to six nitrogen atoms of the two ThPybox ligands as well as three water molecules. The water molecules were most likely incorporated through the solvent. The Eu(III)-N distances are in the range 2.519-2.572 Å and the Eu(III)-O distances are in the range 2.434-2.484 Å, as shown in Table S2 below.

TABLE S2

Selected bond lengths (Å) and angles (°) for the 2:1 ThPybox-Eu(III) complex.

| Eu(1)—O(3)#1 | 2.439(4) |
|---|---|
| Eu(1)—O(3) | 2.439(4) |
| Eu(1)—O(4) | 2.485(6) |
| Eu(1)—N(2)#1 | 2.527(5) |
| Eu(1)—N(2) | 2.527(5) |
| Eu(1)—N(3)#1 | 2.534(5) |
| Eu(1)—N(3) | 2.534(5) |
| Eu(1)—N(1) | 2.575(4) |
| Eu(1)—N(1)#1 | 2.575(4) |
| O(3)#1—Eu(1)—O(3) | 137.75(19) |
| O(3)#1—Eu(1)—O(4) | 68.87(10) |
| O(3)—Eu(1)—O(4) | 68.87(10) |
| O(3)#1—Eu(1)—N(2)#1 | 79.88(14) |
| O(3)—Eu(1)—N(2)#1 | 88.78(15) |
| O(4)—Eu(1)—N(2)#1 | 74.14(11) |
| O(3)#1—Eu(1)—N(2) | 88.78(15) |
| O(3)—Eu(1)—N(2) | 79.88(14) |
| O(4)—Eu(1)—N(2) | 74.14(11) |
| N(2)#1—Eu(1)—N(2) | 148.3(2) |
| O(3)#1—Eu(1)—N(3)#1 | 143.08(14) |
| O(3)—Eu(1)—N(3)#1 | 74.39(15) |
| O(4)—Eu(1)—N(3)#1 | 137.37(11) |
| N(2)#1—Eu(1)—N(3)#1 | 126.50(15) |
| N(2)—Eu(1)—N(3)#1 | 78.90(15) |
| O(3)#1—Eu(1)—N(3) | 74.39(15) |
| O(3)—Eu(1)—N(3) | 143.08(14) |
| O(4)—Eu(1)—N(3) | 137.37(11) |
| N(2)#1—Eu(1)—N(3) | 78.90(15) |
| N(2)—Eu(1)—N(3) | 126.50(15) |
| N(3)#1—Eu(1)—N(3) | 85.3(2) |
| O(3)#1—Eu(1)—N(1) | 71.81(14) |
| O(3)—Eu(1)—N(1) | 133.44(14) |
| O(4)—Eu(1)—N(1) | 121.40(10) |
| N(2)#1—Eu(1)—N(1) | 137.29(15) |
| N(2)—Eu(1)—N(1) | 63.26(14) |
| N(3)#1—Eu(1)—N(1) | 71.55(15) |
| N(3)—Eu(1)—N(1) | 63.25(14) |
| O(3)#1—Eu(1)—N(1)#1 | 133.44(14) |
| O(3)—Eu(1)—N(1)#1 | 71.81(14) |
| O(4)—Eu(1)—N(1)#1 | 121.40(10) |
| N(2)#1—Eu(1)—N(1)#1 | 63.26(14) |
| N(2)—Eu(1)—N(1)#1 | 137.29(15) |
| N(3)#1—Eu(1)—N(1)#1 | 63.25(14) |
| N(3)—Eu(1)—N(1)#1 | 71.55(15) |
| N(1)—Eu(1)—N(1)#1 | 117.2(2) |

Symmetry transformations used to generate equivalent atoms:
1 −x,y,−z + 3/2 #2 −x + 2,y,−z + 3/2

The polyhedron around the metal ion is a slightly distorted tricapped trigonal prism with the oxygen of the center water molecule and the pyridine nitrogen atoms as the capping atoms. The packing structure is dominated by hydrogenbonding interactions between the triflate counterions and the water molecules coordinated to Eu(III), weak hydrogen-bonding interactions between the triflate counterions and R-hydrogen atoms on the thiophene rings as well as short contacts between the fluorine and oxazoline oxygen (dashed lines, FIG. 5b).

Figure 5B:
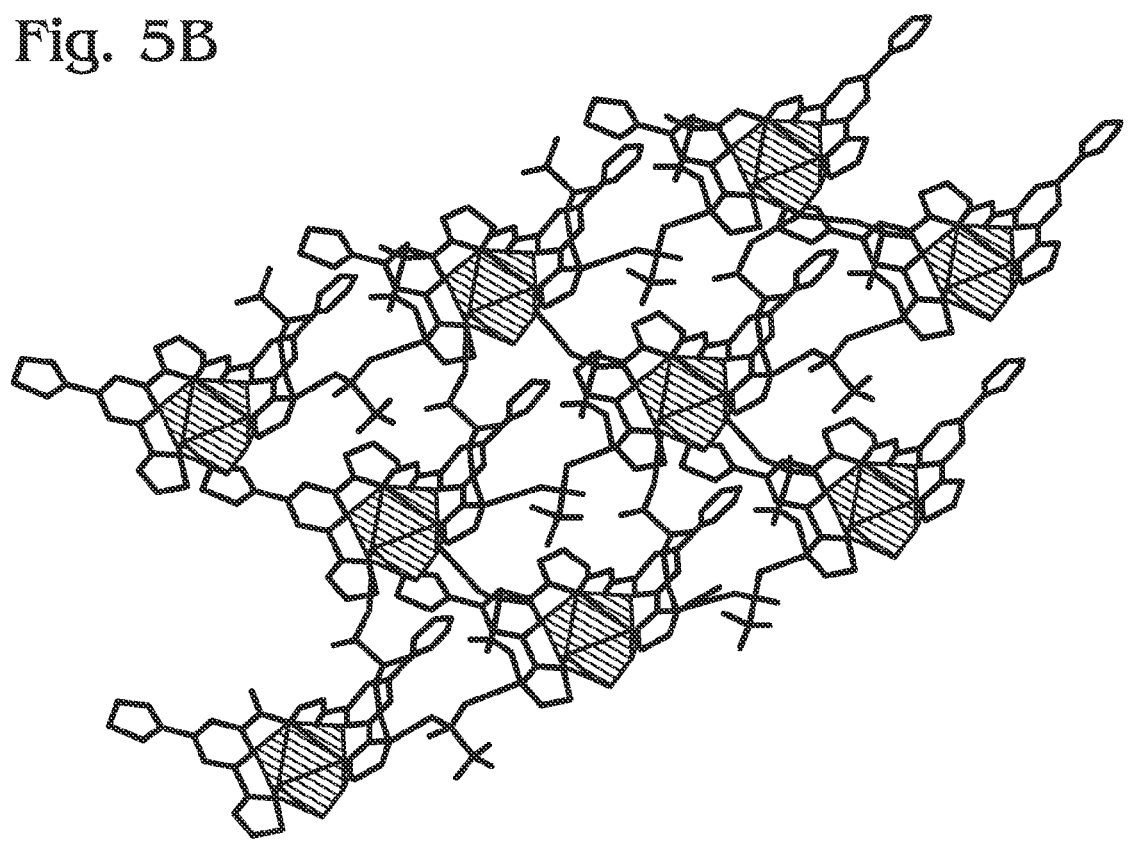
FIG. 5b is a packing diagram with a polyhedral representation of Eu(III) in the complex of $Eu(CF_3SO_3)_3$ with ThPybox, according to an embodiment of the present invention.

As seen in FIG. 5b, a packing diagram is provided with polyhedral representation of Eu(III). Dashed bonds show selected intermolecular interactions of the triflate couteranions. Hydrogen atoms were omitted for clarity. The triflate ions provide for the electrical neutrality of the complex and stitch the complex cations together into a three-dimensional structure via hydrogen bonding.

Figure 6:
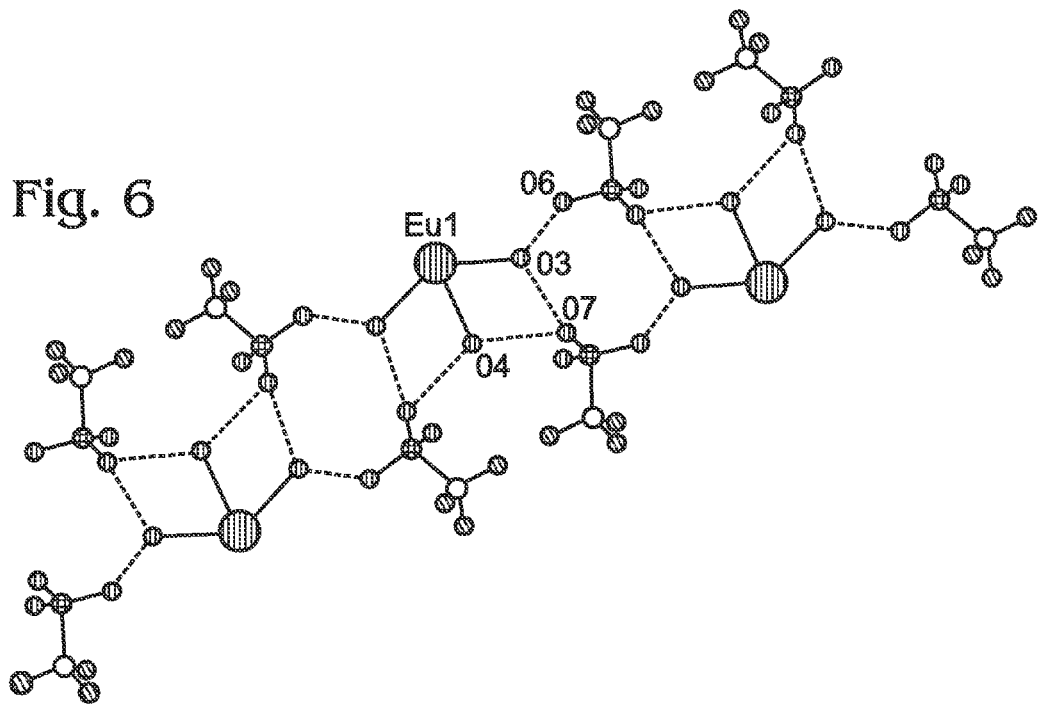
FIG. 6 is a partial ball-and-stick drawing displaying in detail the hydrogen-bonding interactions in the 2:1 ThPybox-Eu(III) complex, according to an embodiment of the present invention.

As seen in FIG. 6, a partial ball-and-stick drawing displaying in detail the hydrogen-bonding interactions in the 2:1 ThPybox-Eu(III) complex is illustrated. Hydrogen-bonding interactions in the range of 2.7272-2.8291 Å (distances -O3-O6 2.7273, O3-O7 2.8291 and O4-O7 2.8014 Å) are seen between the triflate oxygen atoms and the water molecule oxygen atoms.

Figure 7A:
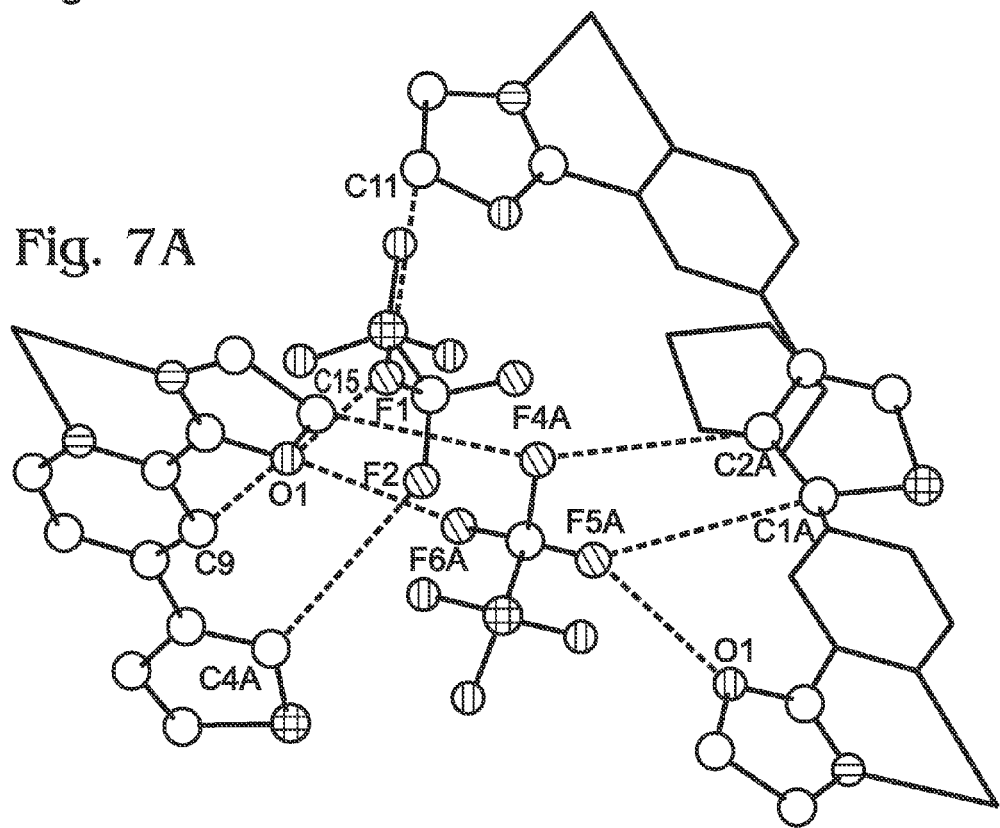
Figure 7A:
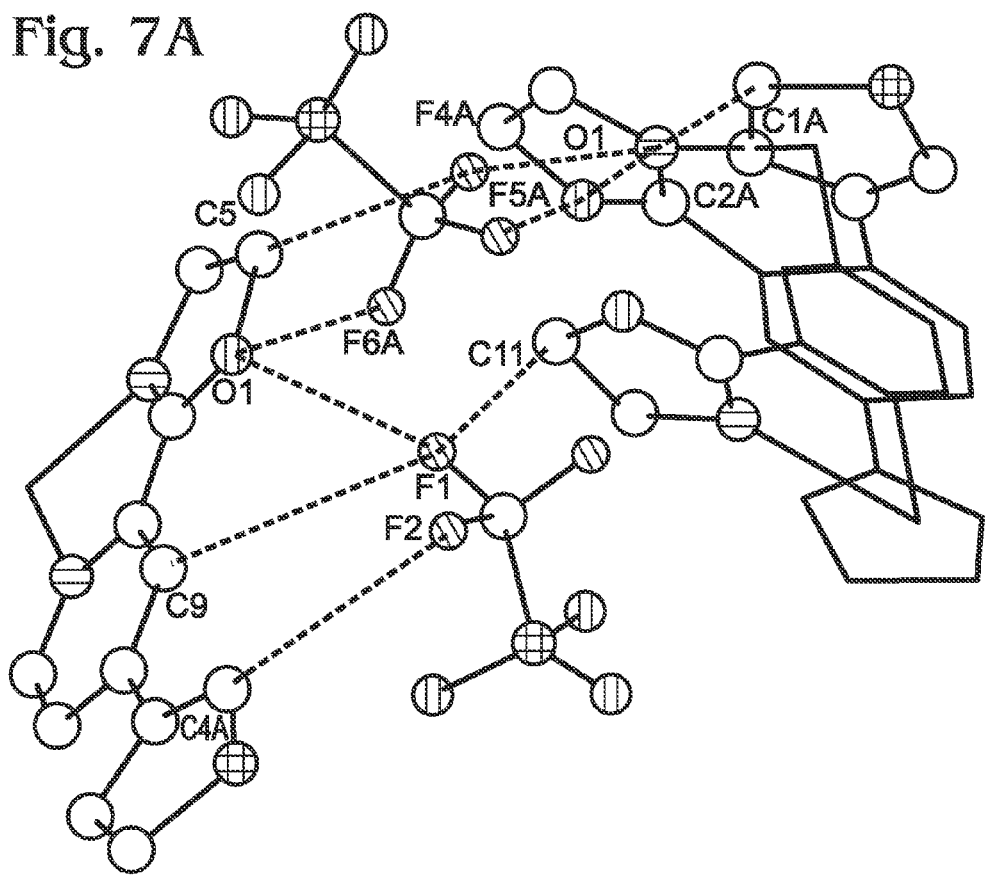

As seen in FIG. 7a-b, partial ball-and-stick drawings showing the F—O short contacts and weak hydrogen bonding interactions C—H—F in the 2:1 ThPybox-Eu(III) complex is illustrated. Selected distances (Å)/angles D-A (o) are F1-O1 2.774, F5A-O1 2.879, F6A-O1 2.867, F1-C9 3.7233/111, F1-C11 3.479/126, F2-C4A 3.651/148, F4A-C2A 3.673/165, F4A-C15 3.502/118, F5A-C1A 3.628/95. Other interactions such as weak hydrogen bonding, as defined by Desiraju (Desiraju, G.; Steiner, T. *The Weak Hydrogen Bond In Structural Chemistry and Biology*; Oxford University Press: New York, 1999; Vol. 9), between fluorine atoms and C—H moieties of the oxazoline or thiophene rings and F—O shorts contacts (Patroniak, V.; Baxter, P. N. W.; Lehn, J.-M.; Hnatejko, Z.; Kubicki, M. *Eur. J. Inorg. Chem.* 2004, 2379-2384; Cantuel, M.; Bernardinelli, G.; Muller, G.; Riehl, J. P.; Piguet, C. *Inorg. Chem.* 2004, 43, 1840-1849) are present in this structure.

These complexes, as well as others with similar pybox ligands, (see FIGS. 13*a-d*, and 21) are highly luminescent in the solid state, as shown by the characteristic red or green color seen when the crystals are held under a handheld UV lamp ($\lambda$=254 nm). When dissolved in methanol or acetonitrile luminescent solutions are obtained. While the 2:1 complex was isolated in the solid state, as described herein, other species are present in solution. To characterize these other species, the following Example describes the titration of ThPybox with Ln(III) nitrates in acetonitrile.

EXAMPLE 8

This Example describes the spectrophotometric titrations of the ThPybox ligand obtained in Example 6 with lanthanide nitrates in acetonitrile. The absorption and emission spectra of the resulting solutions were measured.

All the solutions were prepared in analytical grade acetonitrile at constant ionic strength, I=0.1 M, using $Et_4NCl$. Stock solutions of lanthanide nitrates at 0.01 M, were prepared by dissolving appropriate quantities of Ln$(NO_3)_3 \cdot 6H_2O$ [Ln=Gd(III), Eu(III), Tb(III)] in analytical grade acetonitrile. The solutions were standardized by titration with ethylenediaminetetraacetic acid (EDTA) standardized solution (0.01 M) using xylenol orange as indicator in hexamine buffered solutions (Bassett, J.; Denney, R. C.; Jeffery, G. H.; Mendham, J., Vogel—*Análise Inorgânica Quantitativa*, $4^{th}$ ed.; Editora Guanabara: 1978). The stock solution of the ThPybox ligand obtained in Example 6 was also prepared at 0.01 M concentration in acetonitrile. For titrations and photophysical measurements, these stock solutions were diluted as needed.

25 ml of 1×10$^{-4}$ M ThPybox ligand was titrated against standardized metal nitrate solution, under argon. After each addition of the metal and a delay of 10 minutes, the absorption/emission spectrum was measured. Each titration run had 25-40 data points to allow for a good fitting. It was also ensured that a wide range of ligand-to-metal ion stoichiometric ratios was considered. Three repeat titrations were performed for each system to account for experimental errors. Refinement of stability constants was performed using the HYPERQUAD2006 (Gans, P.; Sabatini, A.; Vacca, A., *Talanta* 1996, 43, (10), 1739-1753) software package. For the refinement of the UV data, only points in the range 240-330 nm were utilized which gave the best fit of the experimental data. In the case of the fluorescence titrations, only the main emission peaks of Eu(III) and Tb(III) were utilized for fitting the data.

Results of these speciation studies are summarized in Table 1 below, and are consistent with the formation of 1:1, 2:1, and 3:1 species in solution.

TABLE 1

Speciation Data of Ln(III)(NO$_3$)$_3$ with ThPybox in Acetonitrile Obtained by Absorption and Emission Titrations[a]

| Ln (III) | method | log $\beta_{11}$ | log $\beta_{21}$ | log $\beta_{31}$ |
|---|---|---|---|---|
| Eu | absorption | 5.70 ± 0.07 | 10.70 ± 0.20 | 15.38 ± 0.10 |
|    | emission   | 5.15 ± 0.18 | 10.09 ± 0.11 | 14.34 ± 0.20 |
|    | average    | 5.43 ± 0.19 | 10.40 ± 0.23 | 14.86 ± 0.22 |
| Tb | absorption | 5.01 ± 0.17 | 9.10 ± 0.11  | 13.38 ± 0.14 |
|    | emission   | 4.75 ± 0.09 | 9.09 ± 0.07  | 12.10 ± 0.20 |
|    | average    | 4.88 ± 0.19 | 9.10 ± 0.13  | 12.74 ± 0.24 |

[a]Values are the average of at least three measurements with each technique. Sample absorption titration shown in FIG. 8.

The stability constants were obtained through independent absorption and emission titrations and are similar for both ions, with the Eu(III) species being slightly more stable.

Figure 8:
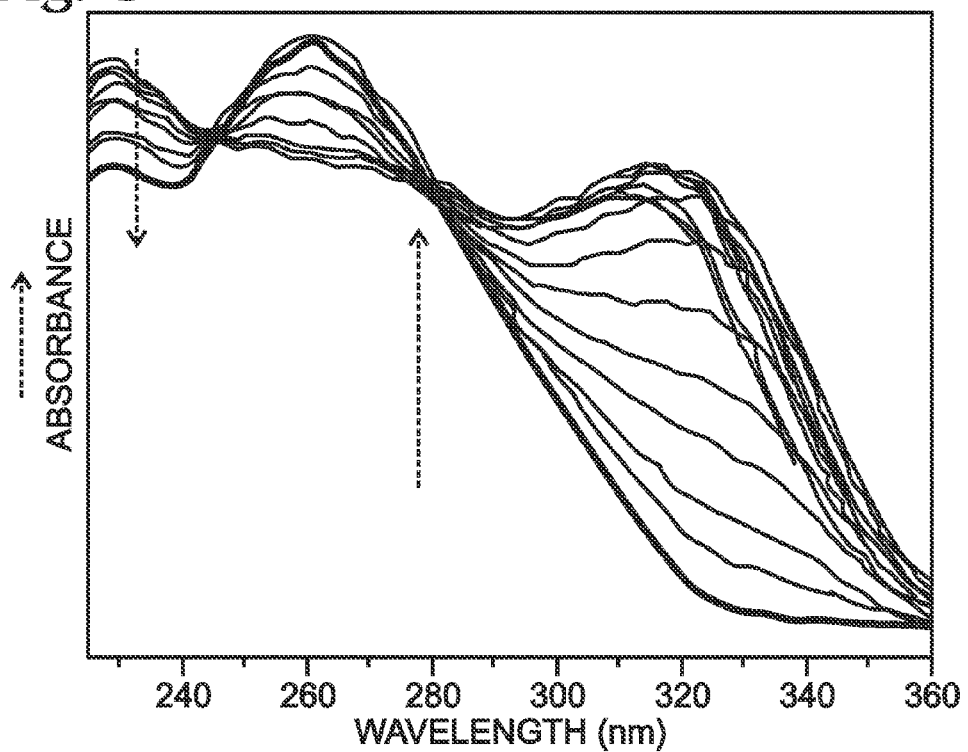
FIG. 8 is a graphical illustration showing sample UV/vis titration of ThPybox with Eu(III) in acetonitrile at I=0.1 M ($Et_4NCl$), for the speciation and determination of stability constants of the species formed in solution by UV/vis titration, according to an embodiment of the present invention.

As referenced in Table 1, FIG. 8 shows sample UV/vis titration of ThPybox with Eu(III) in acetonitrile at I=0.1 M (Et$_4$NCl), for the speciation and determination of stability constants of the species formed in solution by UV/vis titration. The arrows indicate the direction of change in the absorption spectrum of the ligand ThPybox with increasing concentration of Eu(III). Only data points in the range 240-330 nm were utilized for the data fitting.

Figure 9:
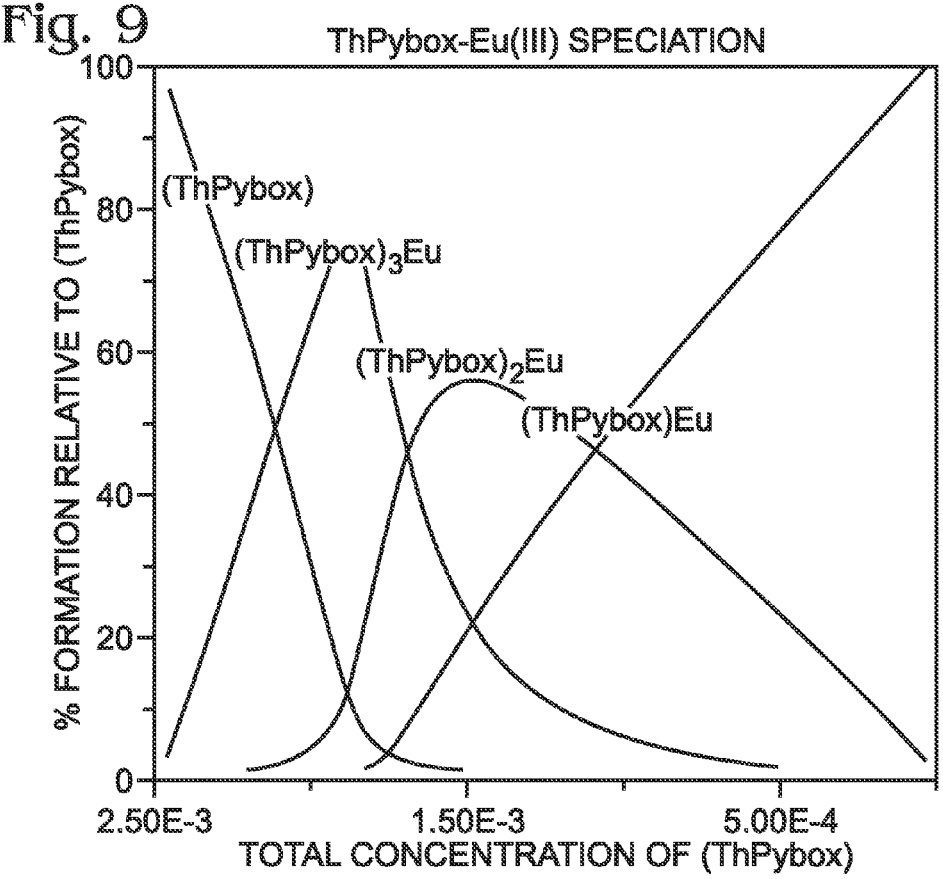
FIG. 9 is a speciation diagram illustrating the dissociation and formation of 3:1, 2:1, and 1:1 species during titration of a solution of ThPybox with Eu(III) in acetonitrile, according to an embodiment of the present invention.

As seen in FIG. 9, a speciation diagram is shown illustrating the dissociation and formation of 3:1, 2:1, and 1:1 species during titration of a solution of ThPybox with Eu(III) in acetonitrile. Through the use of speciation diagrams (as shown in FIG. 9), conditions for the photophysical measurements were chosen to ensure that the main species in solution was the 3:1 species. These photophysical measurements are described in the following Example.

EXAMPLE 9

This Example describes photophysical measurements of ThPybox in acetonitrile with Ln(CF$_3$SO$_3$)$_3$ (Eu(III) and Tb(III)) in 3:1 stoichiometry.

The solutions for all the photophysical measurements were allowed to equilibrate for 2-3 hours before being used for routine photophysical measurements. For quantum yield measurements, both the absorption and emission/excitation spectra were measured using 0.1 cm path length cells, making sure that while measuring the emission/excitation spectra, the emitted light is at right angle and along the long path length (1 cm). All measurements, except the triplet-state measurements, were performed at 25±0.1° C. The triplet-state measurements were performed at 77 K, as described by Crosby (Crosby, G. A.; Whan, R. E.; Alire, R. M., *J. Chem. Phys.* 1961, 34, 743-8).

In the case of the Eu(III) solutions, a single exponential could be used to fit the decay curve. The Tb(III) solutions could only be fit by a second-order exponential decay. All reported data are the average of at least three independent measurements.

Quantum yields were calculated using Equation 1 below:

$$\Phi_x = \frac{n_x^2 A_{ref} I_{ref} E_x}{n_{ref}^2 A_x I_x E_{ref}} \times \Phi_{ref} \quad (1)$$

$\Phi$ is the quantum yield of sample x and reference ref, n is the refractive index (1.343 in acetonitrile), A the absorbance at the excitation wavelength, I the intensity of the corrected excitation spectrum at the excitation wavelength and E the integrated corrected emission spectrum. The spectra are always corrected for instrumental functions. Quantum yields for the reported solutions were measured against C$_{S3}$[Eu(dipic)$_3$] ($\Phi_{ref}$=24.0%, A$_{279}\approx$0.15, 7.5×10$_{-5}$ M) and C$_{S3}$[Tb(dipic)$_3$] ($\Phi_{ref}$=22.0%, A$_{279}\approx$0.15, 6.5×10$_{-5}$ M) in Tris buffer (0.1 M) as reference standards (Chauvin, A.-S.; Gumy, F.; Imbert, D.; Bünzli, J.-C. G., *Spectroscopy Lett.* 2004, 37(5), 517-532). The excitation wavelengths of the samples were chosen to ensure that there is a linear relationship between the intensity of emitted light and the concentration of the absorbing/emitting species (A≤0.05).

Figure 10:
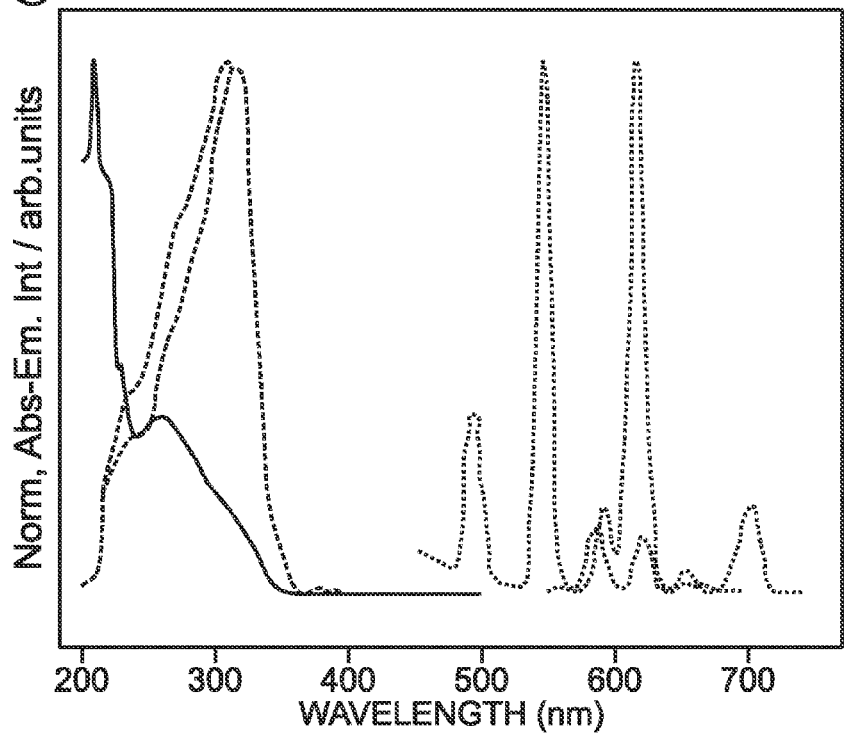
FIG. 10 is a graphical illustration showing absorption (solid), excitation (dashed), and emission (solid) spectra of ThPyboxEu and ThPyboxTb, according to an embodiment of the present invention.

As seen in FIG. 10, absorption (solid), excitation (dashed), and emission (solid) spectra of ThPyboxEu (right trace of emission) and ThPyboxTb (left trace of emission) are illustrated. Absorption, excitation, and emission spectra for both metal ion complexes show that the excitation spectra closely follow the absorption spectrum of the ligand. Further, the emission spectra of both Eu(III) and Tb(III) solutions show the characteristic transitions $^5D_0 \rightarrow {}^7F_J$ (J) 1-4) and $^5D_4 \rightarrow {}^7F_J$ (J) 6-2), respectively.

As a result of almost complete quenching of the ligand centered emission in the case of the Tb(III), an increased background in the 450 to 500 nm region is seen. This translates into a quantum yield of emission of 58.6% for Tb(III), which is lower than the emission efficiency of 76.2% determined for Eu(III) as shown in Table 2 below.

TABLE 2

Photophysical Characterization of Ln(III)(NO$_3$)$_3$ with ThPybox in Acetonitrile in 3:1 Stoichiometry[a]

| complex | ThPyboxEu | ThPyboxTb |
| --- | --- | --- |
| Φ[%][b] | 76.2 ± 6.6 | 58.6 ± 4.1 |
| τ[ms] | 2.097 ± 0.081 | 0.367 ± 0.032 |
|  |  | 0.019 ± 0.002 |
| $^1$S[cm$^{-1}$][c] | 28310 (28,610) | |
| $^3$T[cm$^{-1}$][c] | 21080 (21,080) | |

[a][L] = 3[Ln(III)] ≈ 1 × 10$^{-6}$ M.
[b]Average of at least three measurements with different experimental conditions.
[c]Measured in a solution with Ln = Gd at 77 K,[24] data in parenthesis is uncoordinated ligand.

However, both values are high and are accompanied by long luminescence lifetimes of ~2 ms for the Eu(III) and 367 µs for the Tb(III) species.

The lifetime of the red emission could be determined from a single-exponential fitting of the decay curve and is consistent with the presence of one major luminescent species. In the case of the green emission, a double exponential had to be utilized.

Figure 11:
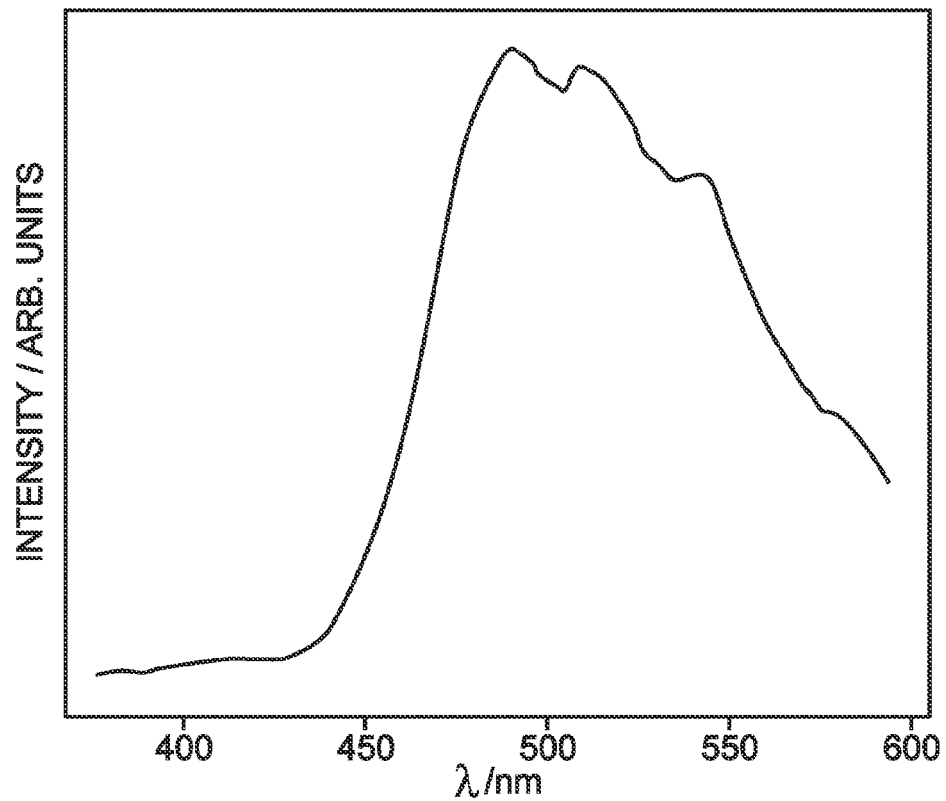
FIG. 11 is a graphical illustration showing triplet emission spectrum of ThPyboxGd in acetonitrile at about 77K, according to an embodiment of the present invention.

As seen in FIG. 11, a closer inspection of the triplet emission spectrum of the ThPybox ligand in acetonitrile at 77 K reveals that the second component corresponds to residual ligand emission. This residual ligand emission, as mentioned above, is not completely quenched by the Tb(III) and overlaps with the transitions of the metal ion.

As shown in the foregoing Examples, ThPybox is a highly efficient sensitizer of Eu(III) and Tb(III) luminescence, as reflected in the high emission quantum yields of luminescence, which in the case of Eu(III) is up to three times as high as previously reported for other complexes. Further, the versatile chemistry of these ligands allows tuning of the sensitization ability and tailoring of the Ln(III) complex properties for specific applications. As such, pybox and its derivatives are a promising new class of antennas for lanthanide ion emission.

EXAMPLE 10

Figure 12:
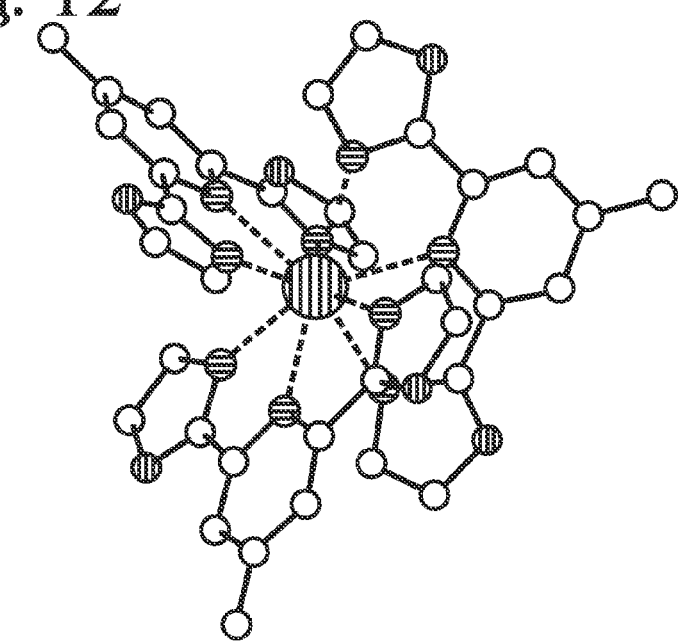
FIG. 12 is a high level schematic illustrating the structure of $[Eu(pybox-derivative)_3]^{3+}$ calculated with CaChe (MOPAC, AM1 parameters), according to an embodiment of the present invention.

This example describes the modeling of a 3:1 complex of the sensitizing moiety, pybox substituted with thiophene-phenyl-thiophene calculated with CaChe, (*Quantum CaChe*, 6.1.12; Fujitsu Ltd.) with Eu(III). The resultant [Eu(pybox-derivatized)$_3$]$^{3+}$ structure calculated with CaChe, is shown in FIG. 12. In this figure the thiophene-phenyl-thiophene moieties have been removed for clarity.

Since the pybox-based ligands studied by Aspinall and Desimoni have bulky substituents on the carbon adjacent to the oxazoline nitrogen atom, a pybox without such substituents was utilized. This unsubstituted pybox was a less crowded chelator, and thus, the 3:1 complexes could be demonstrated in solution.

The calculations performed demonstrate that three ligands can be accommodated around Eu(III), yielding a coordination number of 9 for the metal ion. The calculated Eu—N bond distances are in the range of 2.481 to 2.542 Å and comparable to experimental distances of 2.502 to 2.590 Å, found for the 2:1 complex of Eu(III) with $^i$Pr-pybox studied by Aspinall, where the isopropyl group is attached to the carbon adjacent to the oxazoline nitrogen.

EXAMPLE 11

This example describes the synthesis of pybox and pybox derivatives, the isolation of additional novel complexes of pybox with Ln(III) ions, as well as the resulting sensitization and luminescence. The details of the structural and photophysical characterizations are shown and described in FIGS. 13-21.

Figure 13C:
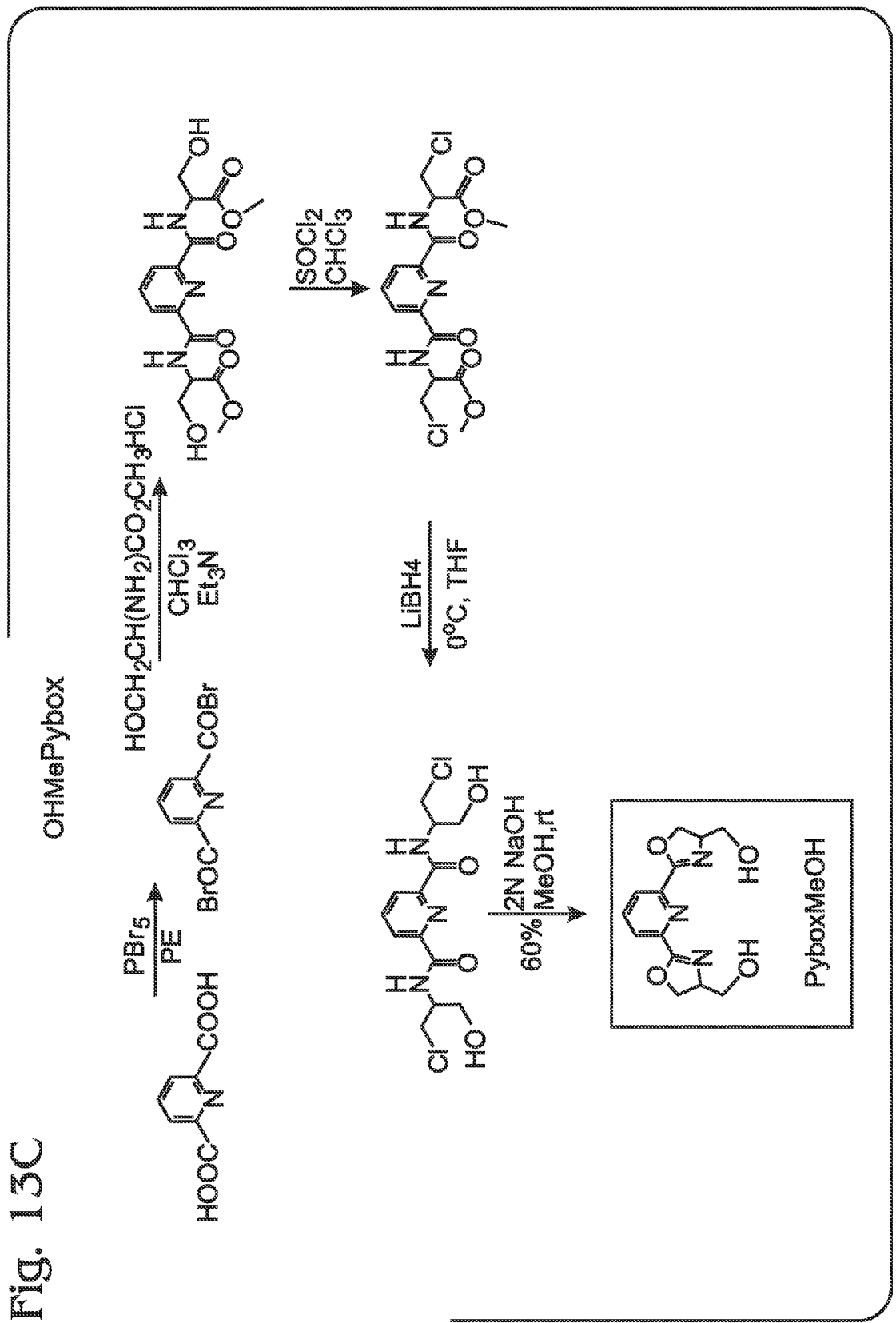

As seen in FIGS. 13*a*-*c*, high level schematics illustrating ligand synthesis (e.g., pybox and pybox derivatives), according to an embodiment of the present invention is shown. For example, the synthesis of ThPybox (which is shown and described above in Examples 1-6), as well as BrPybox (see Examples 1-4) is shown.

OMePybox can be synthesized by following Examples 1-3 above, followed by cyclization which occurs upon treatment with KOH/MeOH to yield the target compound.

2-ThPybox can be synthesized in a similar fashion to ThPybox. For 2-ThPybox, tributyltinthiophen-2-yl is utilized instead of the thiophene derivatized at the 3-position.

PyboxOH can be synthesized in a similar fashion to OMe-Pybox. For PyboxOH, cyclization occurs upon treatment with KOH/water to yield the target compound.

ThPhThPybox can be synthesized by following Examples 1-4 above to yield BrPybox. The BrPybox is treated with the boronic acid derivative of 3,5-bithiophen-3-ylbenzene in the presence of a Pd(0) catalyst and toluene to yield the target compound.

PyboxMeOH can be synthesized by treating pyridine-2,6-dicarboxylic acid with thionyl chloride under nitrogen under heating and stirring to yield the acid chloride. The thionyl chloride is removed under reduced pressure and the compound is added without further purification to a solution of L-serine methyl ester hydrochloride in chloroform in the presence of triethylamine as the base. The resulting mixture is stirred at room temperature overnight. After removal of a white precipitate the filtrate is evaporated to dryness to yield the amid alcohol. This amid alcohol is treated with thionyl chloride to yield the amid chloride derivative. This derivative is cyclized in the presence of LiBH$_4$ in THF under stirring to yield the target compound. Alternatively, the amid chloride can also by cyclized in the presence of NaOH/methanol.

Underivatized Pybox, as shown in FIG. 13*b*, can be synthesized from pyridine-2,6-dicarboxylic acid. This compound is treated with thionyl chloride to yield the acid chloride. Treatment of the acid chloride with 2-chloroethanamine hydrochloride in the presence of a base, such as sodium carbonate, yields the uncyclized carboxamide. Cyclization in the presence of KOH/MeOH yields the target compound.

Synthesis of the above referenced ligands with lanthanide metals to yield the pybox/pybox derivative and ligand metal complexes will now be described. Pybox and any of its derivatives can be stirred with Ln(NO$_3$)$_3$ (Ln=Eu or Tb) in methanol, acetonitrile or Ln(CF$_3$SO$_3$)$_3$ (Ln=Eu, Tb) in chloroform/methanol, or acetonitrile (with the desired stoichiometry) to yield, (after a few days), X-ray quality crystals of the 1:1, 2:1 or 3:1 species. The crystals are removed from the mother liquor and mounted on a glass fiber for X-ray crystallographic analysis, as described above in Example 7 (A representative synthesis and xray crystallographic analysis is also described in Example 7, supra).

Figure 13D:
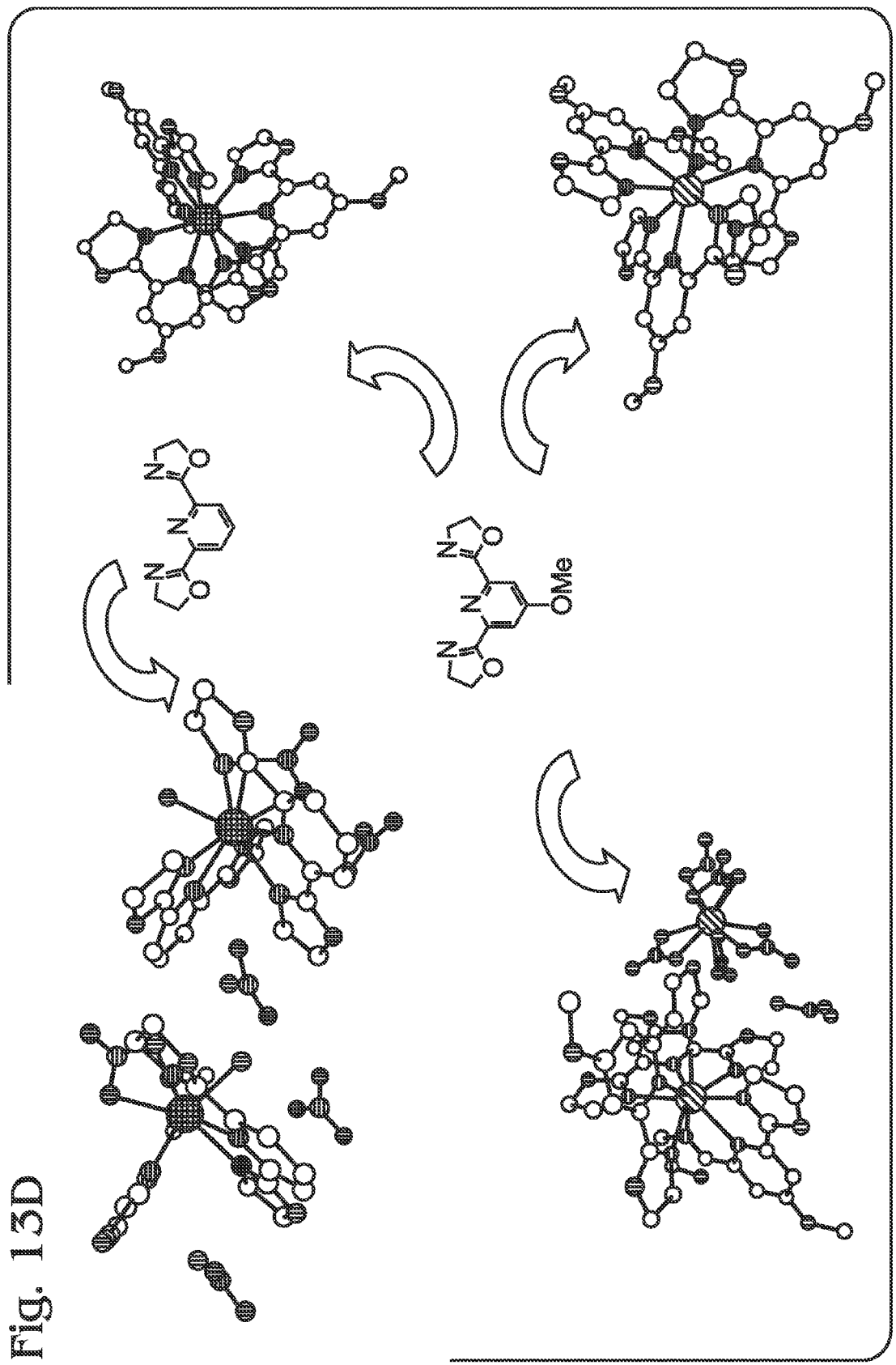
FIG. 13d is a ball and stick diagram illustrating the isolated crystal structures of particular pybox complexes, according to an embodiment of the present invention.

FIG. 13d shows a ball and stick diagram illustrating the isolated crystal structures of particular pybox complexes, according to an embodiment of the present invention. These pybox complexes include pybox with Eu in 2:1 stoichiometry, OMePybox with Eu and Tb in 3:1 stoichiometry, and OMePybox with Eu in 3:2 stoichiometry.

As seen in FIG. 14, a high level schematic illustrating a BrPybox-Eu(III) complex is shown.

Figure 15:
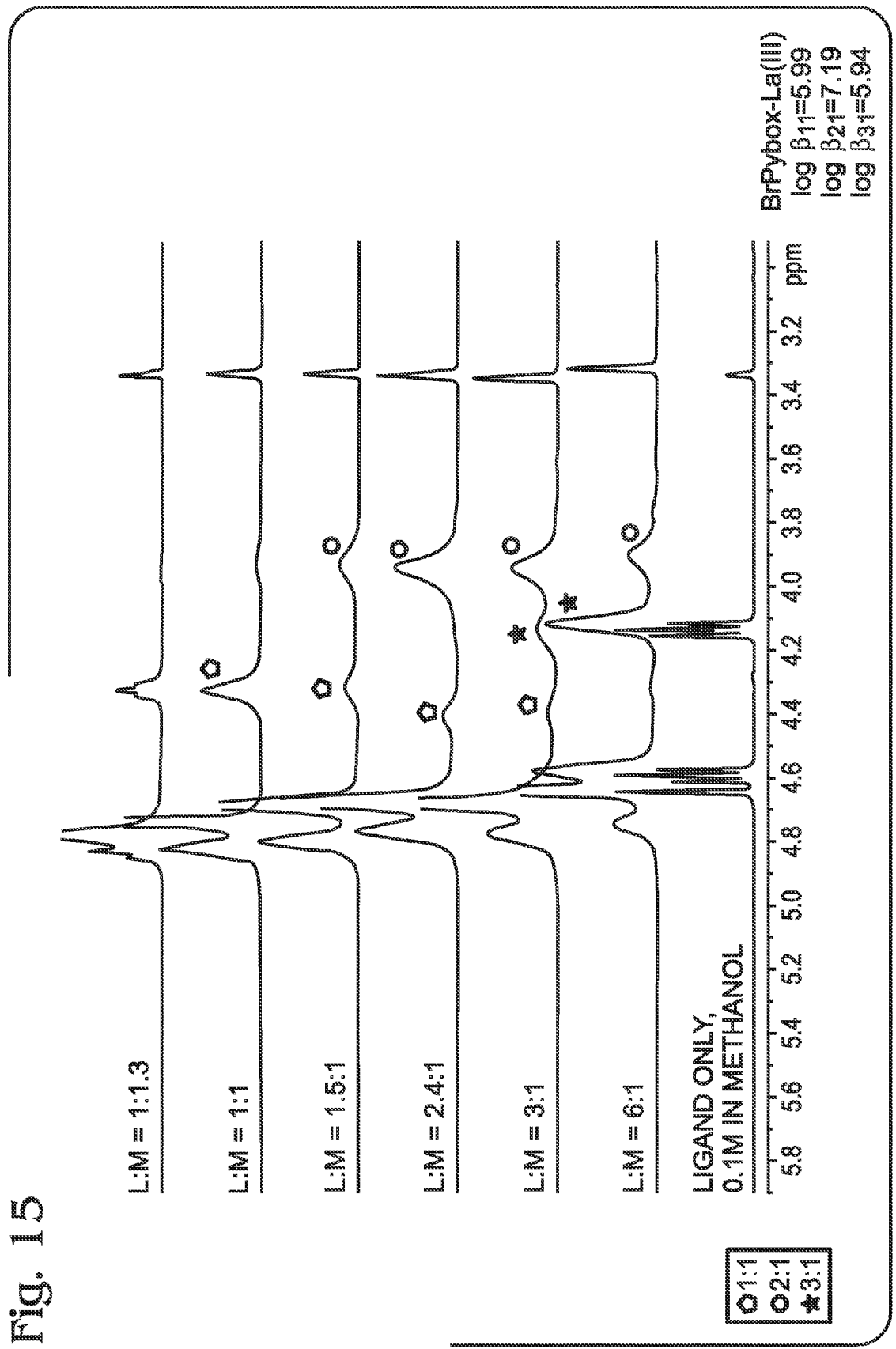
FIG. 15 is a graphical illustration of NMR titration of the BrPybox-La(III) complex for the speciation and determination of stability constants of the species formed in solution by NMR titration, according to an embodiment of the present invention.

As seen in FIG. 15, a graphical illustration of NMR titration of a BrPybox-La(III) complex for the speciation and determination of stability constants of the species formed in solution by NMR titration is shown.

Figure 16:
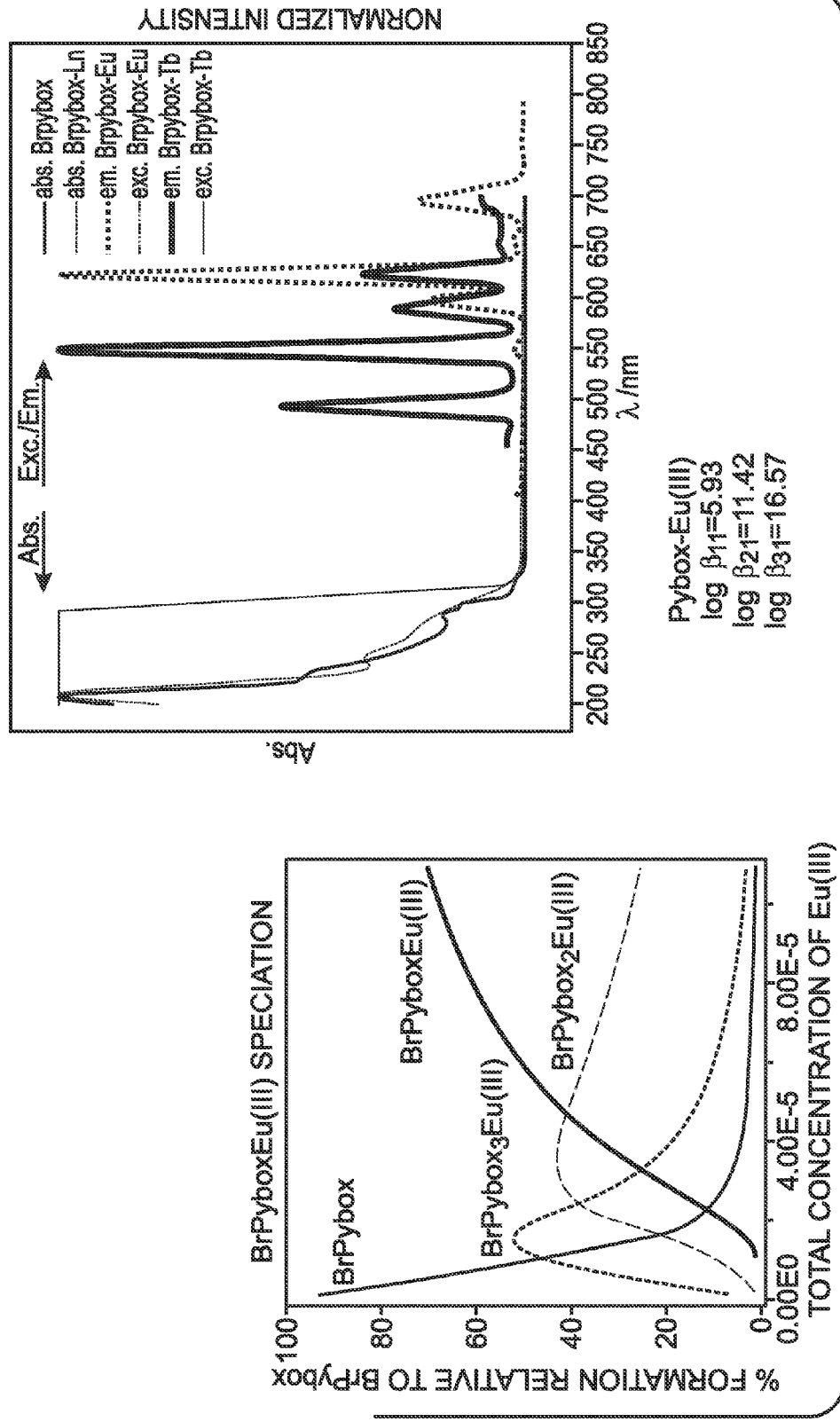
FIG. 16 is a graphical illustration of fluorescence ("FL") and speciation of the BrPybox-La(III) complex for the determination of stability constants of the species formed in solution by FL, according to an embodiment of the present invention.

As seen in FIG. 16, a graphical illustration of fluorescence ("FL") and speciation of the BrPybox-La(III) complex for the determination of stability constants of the species formed in solution by FL is shown.

As seen in FIG. 17, a graphical illustration of the blue fluorescence at λ~430 nm of a pybox ligand derivatized with thiophene at the para position of the pyridine ring is shown.

Figure 18:
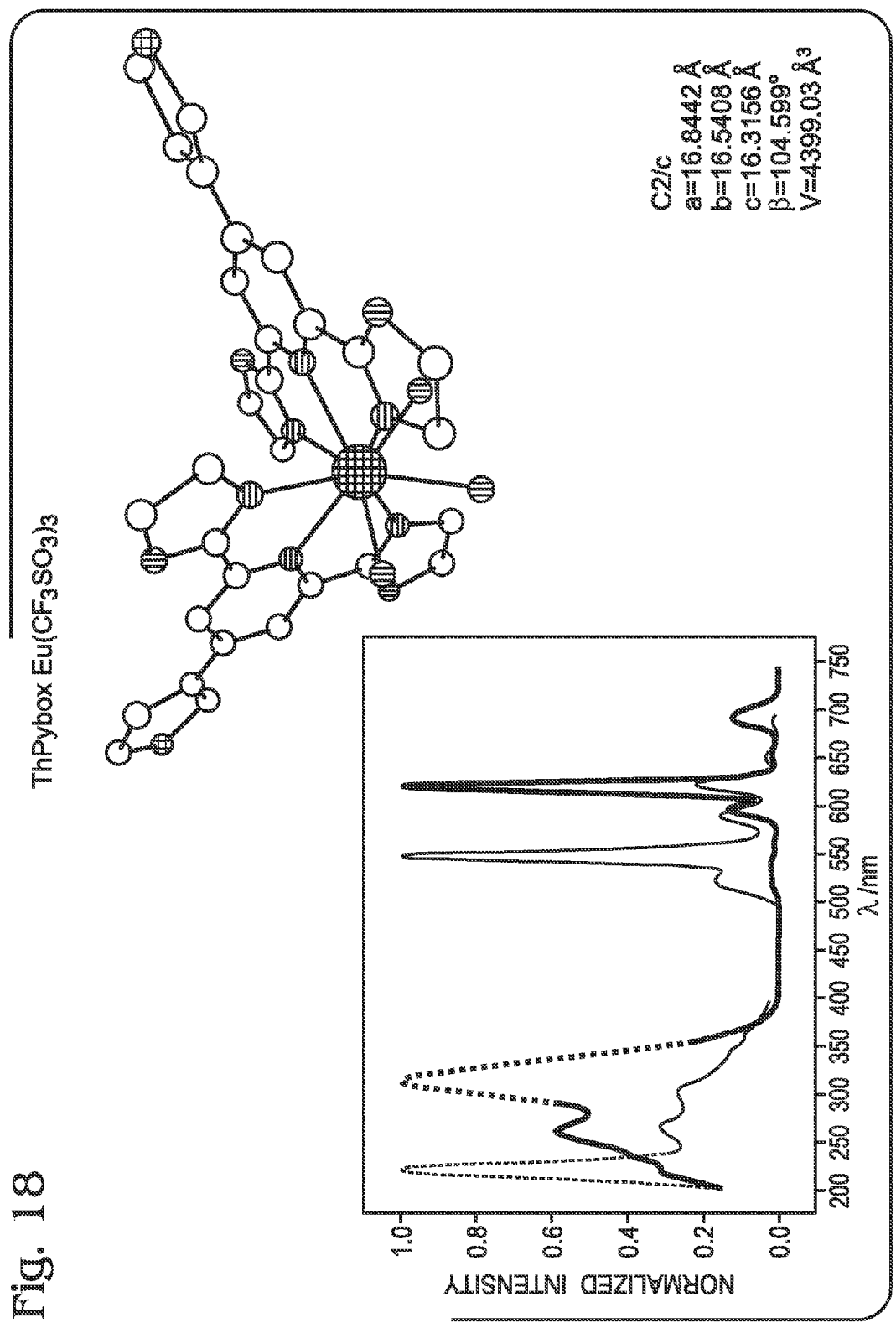
FIG. 18 is an illustration of the crystal structure of a Eu(III) complex with thiophene-derivatized pybox, and a graphical illustration of the excitation and emission spectra of solutions with Eu(III) and Tb(III), according to an embodiment of the present invention.

As seen in FIG. 18, an illustration of the crystal structure of an Eu(III) complex with thiophene-derivatized pybox and a graphical illustration of the excitation and emission spectra of solutions with Eu(III) and Tb(III) is shown.

Figure 19:
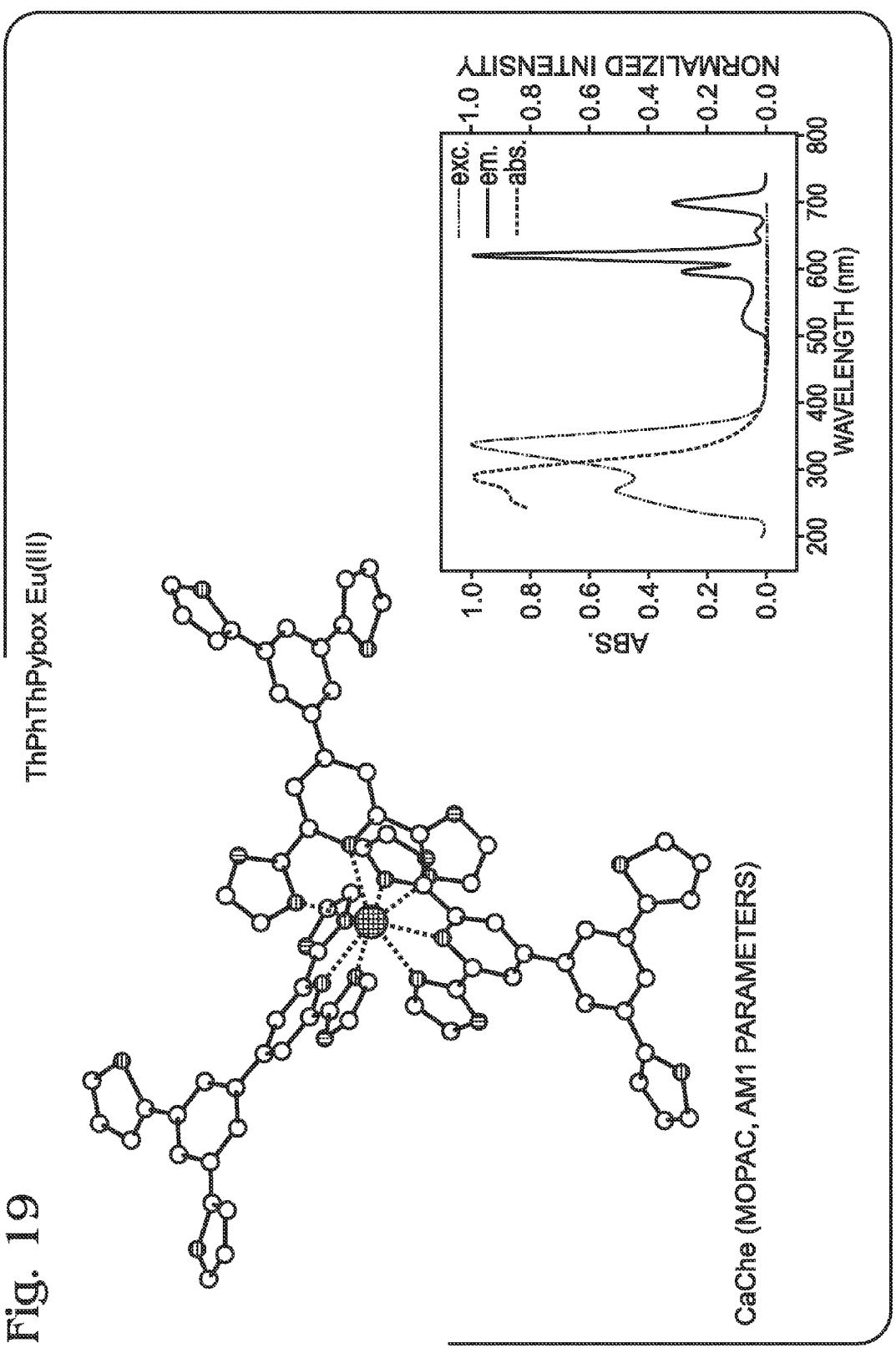
FIG. 19 is an illustration of a calculated structure of Eu(III) complex with thiophene-phenyl-thiophene-derivatized pybox, and a graphical illustration of the excitation and emission spectra of a solution of Eu(III) with this ligand as sensitizer, according to an embodiment of the present invention.

As seen in FIG. 19, an illustration of a calculated structure of Eu(III) complex with thiophene-phenyl-thiophene-derivatized pybox and a graphical illustration of the excitation and emission spectra of a solution of Eu(III) with this ligand as sensitizer is shown.

Figure 20:
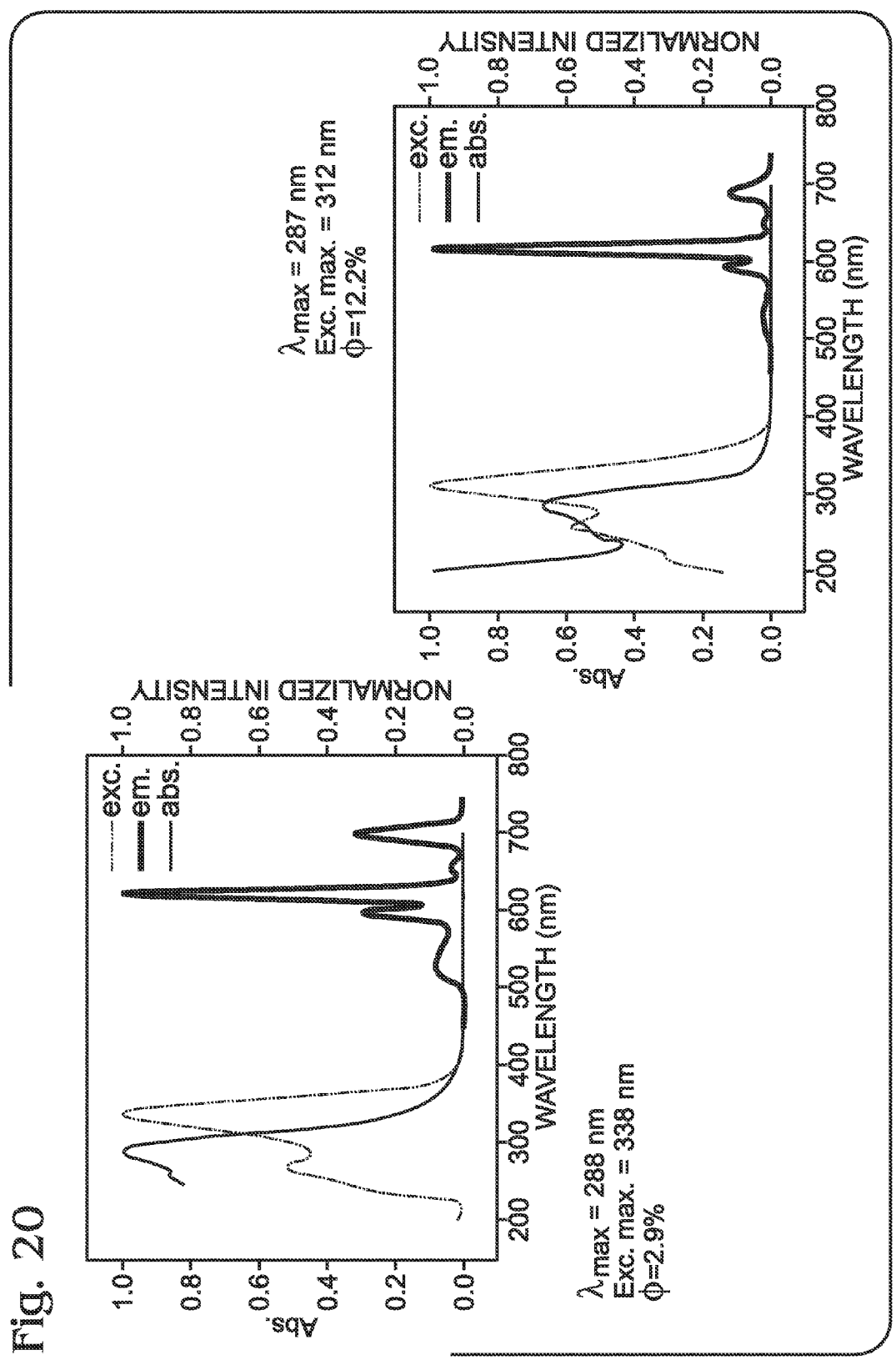
FIG. 20 is a graphical illustration of a comparison between excitation and emission spectra of Eu(III) solutions with thiophene-phenyl-thiophene-derivatized pybox and thiophene-phenyl-thiophene derivatized with pyridine-bisamide, according to an embodiment of the present invention.

As seen in FIG. 20, a graphical illustration of a comparison between excitation and emission spectra of Eu(III) solutions with thiophene-phenyl-thiophene-derivatized pybox and thiophene-phenyl-thiophene derivatized with pyridine-bis-amide is shown. This graphical illustration shows that the latter ligand is better suited for Eu(III) sensitization, as the quantum yield is higher.

As seen in FIG. 21, a table representation illustrating speciation and photophysics of 3:1 complexes of various Pybox derivatized ligands (including BrPybox and MeOPybox) complexed with Ln (III) metal ions (including Eu and Tb) is shown.

In particular, the quantum yields of emission, lifetimes of the excited state, and the energies of singlet and triplet states of the ligands are shown.

The results show that the pybox ligand is especially versatile, as it can be derivatized at the carbon atoms indicated with arrows in FIG. 3, and can be attached, for example, to proteins or to oligonucleotides. Specifically, the results show that further derivatization of pybox at the para-carbon of pyridine and the alpha-carbon of oxazoline N is possible. This provides for additional binding groups and tuning of ligand energy levels. This derivatization of pybox provides for triplet state energy lowering in the case where the pyridine para-position is derivatized with thiophene.

The results also show that the chelating ligands, discussed herein, show higher stability in solution than previously utilized aromatic carboxylates (results not shown).

The results provide evidence of 1:1, 2:1 and 3:1 species in solution and in the solid state.

Moreover, the results show that the ThPhTh backbone has lower singlet and triplet states and leads to blue luminescence of the ligands, but non-linear geometry allows for ISC and sensitization.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A luminescent lanthanide metal complex comprising a metal ion of the lanthanide series and a metal chelating ligand comprising at least one moiety derived from pyridine-2,6-bis(oxazoline), wherein said at least one moiety derived from pyridine-2,6-bis(oxazoline) has the following formula:

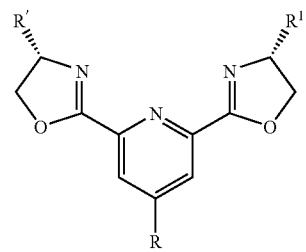

where R'=H, and R=a five membered heterocycle, wherein said heterocycle is thiophen-3-yl.

2. The luminescent lanthanide metal complex of claim 1, wherein said lanthanide metal ion comprises a metal ion selected from the group consisting of europium, terbium, lanthanum, and thulium.

* * * * *